United States Patent
Ding et al.

(10) Patent No.: US 10,626,107 B2
(45) Date of Patent: Apr. 21, 2020

(54) CRYSTAL FORM, SALT TYPE OF SUBSTITUTED 2-HYDRO-PYRAZOLE DERIVATIVE AND PREPARATION METHOD THEREFOR

(71) Applicant: CHIA TAI TIANQING PHARMACEUTICAL GROUP CO., LTD., Lianyungang, Jiangsu (CN)

(72) Inventors: Charles Z. Ding, Shanghai (CN); Shuhui Chen, Shanghai (CN); Lihong Hu, Shanghai (CN); Zhaobing Xu, Shanghai (CN); Yingchun Liu, Shanghai (CN); Bingjie Ren, Shanghai (CN); Weidong Li, Shanghai (CN); Zongbin Li, Shanghai (CN); Rui Zhao, Jiangsu (CN); Xiquan Zhang, Jiangsu (CN)

(73) Assignee: CHIA TAI TIANQING PHARMACEUTICAL GROUP CO., LTD., Jiangsu (CN)

( * ) Notice: Subject to any disclaimer, the term of this patent is extended or adjusted under 35 U.S.C. 154(b) by 0 days.

(21) Appl. No.: 16/331,915

(22) PCT Filed: Sep. 8, 2017

(86) PCT No.: PCT/CN2017/101067
§ 371 (c)(1),
(2) Date: Mar. 8, 2019

(87) PCT Pub. No.: WO2018/045993
PCT Pub. Date: Mar. 15, 2018

(65) Prior Publication Data
US 2019/0194168 A1  Jun. 27, 2019

(30) Foreign Application Priority Data
Sep. 9, 2016 (CN) .......................... 2016 1 0814752

(51) Int. Cl.
*C07D 401/14* (2006.01)
*A61K 31/506* (2006.01)
*A61P 35/00* (2006.01)

(52) U.S. Cl.
CPC .......... *C07D 401/14* (2013.01); *A61K 31/506* (2013.01); *A61P 35/00* (2018.01); *C07B 2200/13* (2013.01)

(58) Field of Classification Search
CPC .................................................... C07D 401/14
See application file for complete search history.

(56) References Cited

U.S. PATENT DOCUMENTS

| 7,855,211 | B2 | 12/2010 | Coates et al. | |
| 9,969,719 | B2* | 5/2018 | Ding | C07D 487/08 |
| 2018/0072707 | A1* | 3/2018 | Ding | C07D 487/08 |

FOREIGN PATENT DOCUMENTS

| CA | 2978363 | 9/2016 |
| CN | 102264725 | 11/2011 |
| WO | 2016/014904 | 1/2016 |
| WO | 2016/141881 | 9/2016 |

OTHER PUBLICATIONS

Berge, Journal of Pharmaceutical Sciences, vol. 66, No. 1, pp. 1-19. (Year: 1977).*
Spring et al. Curr Oncol Rep. ; 21(3): 25, pp. 1-14. (Year: 2019).*
Thangavel et al. Clin Cancer Res; 24(6), pp. 1-14. (Year: 2018).*
ISA/CN, International Search Report for PCT/CN2017/101067 (dated Dec. 14, 2017).

* cited by examiner

*Primary Examiner* — Emily A Bernhardt
(74) *Attorney, Agent, or Firm* — Fish & Richardson P.C.

(57) ABSTRACT

A crystal form and a salt type of a substituted 2-hydro-pyrazole derivative, preparation method therefor, and use of the crystal form and the salt type in preparation of a medicament for treating cancers such as breast cancer, lung cancer and the like.

(I)

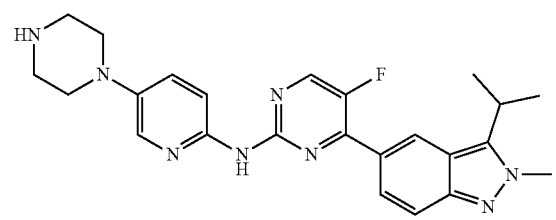

16 Claims, 3 Drawing Sheets

CRYSTAL FORM, SALT TYPE OF SUBSTITUTED 2-HYDRO-PYRAZOLE DERIVATIVE AND PREPARATION METHOD THEREFOR

CROSS REFERENCE TO RELATED APPLICATIONS

This application is a national phase filing under 35 U.S.C. § 371 of International application number PCT/CN2017/101067, filed Sep. 8, 2017, which claims priority from Chinese application number 201610814752.0, filed Sep. 9, 2016. The entire contents of the prior applications are incorporated herein by reference in their entirety.

TECHNICAL FIELD

The present disclosure relates to a crystal form and a salt type of a substituted 2-hydro-pyrazole derivative and a preparation method therefor, and further comprises use of the crystal form and the salt type in preparation of a drug for treating breast cancer and other cancers.

BACKGROUND

The regulation of the cell cycle is mainly influenced by a series of serine/threonine kinases. Such serine/threonine kinases are also called cyclin-dependent kinases (CDKs), and they promote the progression of the cell cycle, the transcription of the genetic information and the normal division and proliferation of cells by binding to their corresponding cyclins which are regulatory subunits. CDK4/6 is a key regulator of the cell cycle and is capable of triggering the transition of the cell cycle from the growth phase (G1 phase) to the DNA replication phase (51 phase). During the cell proliferation, a complex formed by Cyclin D and CDK4/6 is capable of phosphorylating the retinoblastoma protein (Rb). Once the tumor suppressor protein Rb is phosphorylated, its transcription factor E2F which binds tightly to the tumor suppressor protein Rb in an unphosphorylated state may be released. The activation of E2F further transcribes, which promotes the cell cycle to pass the restriction point (R point) and proceed from the G1 phase to the S phase, leading to the cycle of cell proliferation. Therefore, inhibiting CDK4/6 from forming the Cyclin D-CDK4/6 complex is capable of blocking the progression of the cell cycle from the G1 phase to the S phase, thereby achieving the purpose of inhibiting the tumor proliferation. In estrogen receptor positive (ER+) breast cancer (BC), CDK4/6 is frequently overactive while CDK4/6 is a key downstream target of ER signaling. Preclinical data indicates that the dual inhibition of CDK4/6 and estrogen receptor (ER) signaling has a synergistic effect and is capable of inhibiting the growth of estrogen receptor positive (ER+) breast cancer (BC) cells in the G1 phase.

CDK4/6 as a target is a highly competitive field of research and development. Pietzsch summarized the progress in this field in 2010 (Mini-Rev. Med. Chem. 2010, 10, 527-539). Malorni also summarized the research results of the latest CDK4/6 inhibitors in the preclinical and clinical studies of breast cancer in 2014 (Curr. Opin. Oncol. 2014, 26, 568-575). Extensive research efforts on CDK4/6 target contribute to the development of a series of different selective CDK inhibitors, and also lead to the discovery of a few effective and highly selective CDK4/6 inhibitors. Palbociclib (PD0332991) is one of these effective and highly selective CDK4/6 inhibitors. It has entered human clinical trials and is used for the treatment of women with advanced or metastatic estrogen receptor positive (ER+) and human epidermal growth factor receptor 2 negative (HER2-) breast cancer. Based on the mid-term data of the PALOMA-1 trial, Pfizer submitted a new drug application (NDA) for palbociclib to the FDA in August 2014. The FDA approved the request of launching palbociclib in February 2015. Two other CDK4/6 inhibitors, Abemaciclib (LY2835219) and LEE-011, have also begun to recruit patients with cancer for the Phase 3 clinical trials. In addition to being useful in the treatment of breast cancer, these small-molecule heterocyclic compounds are clinically useful in the treatment of a variety of other cancers. These patents include WO2012018540, WO2012129344, WO2011101409, WO2011130232, WO2010075074, WO2009126584, WO2008032157, and WO2003062236.

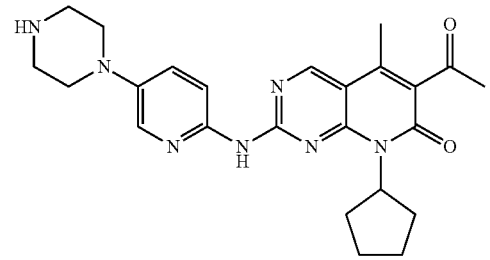

Palbociclib

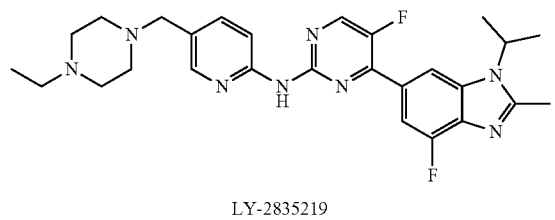

LY-2835219

SUMMARY

The present disclosure provides a maleate salt of the compound of formula (I).

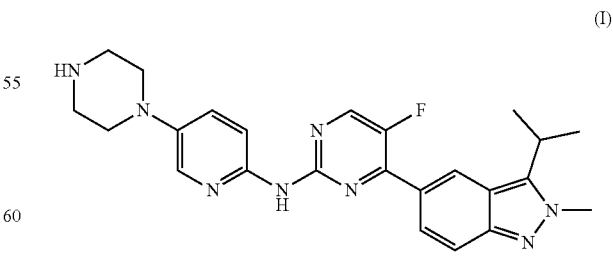

(I)

In some embodiments of the present disclosure, the above-mentioned maleate salt of the compound of formula (I) is as shown in formula (II), wherein x is selected from 0.5 to 2.

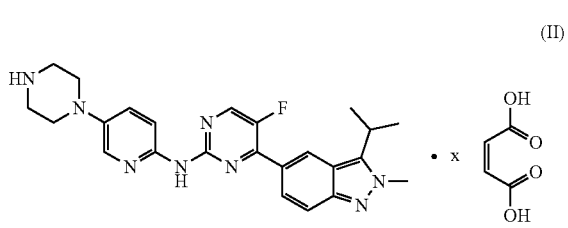

(II)

In some embodiments of the present disclosure, the above-mentioned x is 0.5, 0.6, 0.7, 0.8, 0.9, 1.0, 1.1, 1.2, 1.3, 1.4, 1.5, 1.6, 1.7, 1.8, 1.9, or 2.0.

In some embodiments of the present disclosure, the compound of the above-mentioned formula (II) is compound WX_1, wherein x is 0.8, 0.9, 1, or 1.1.

In some embodiments of the present disclosure, in said compound WX_1, x is 1.

The present disclosure also provides an A crystal form of compound WX_1, and the X-ray powder diffraction spectrum of the A crystal form has characteristic diffraction peaks at the following 2θ angles: 4.69±0.2° and 14.04±0.2°.

In some embodiments of the present disclosure, the X-ray powder diffraction spectrum of the above-mentioned A crystal form has characteristic diffraction peaks at the following 2θ angles: 4.69±0.2°, 9.35±0.2°, 13.28±0.2°, 14.04±0.2°, 16.03±0.2°, 18.74±0.2°, 20.08±0.2°, and 28.25±0.2°.

In some embodiments of the present disclosure, the X-ray powder diffraction spectrum of the above-mentioned A crystal form has characteristic diffraction peaks at the following 2θ angles: 4.69±0.2°, 9.35±0.2°, 10.01±0.2°, 13.28±0.2°, 14.04±0.2°, 16.03±0.2°, 18.74±0.2°, 20.08±0.2°, 23.53±0.2°, 25.11±0.2°, 27.80±0.2°, and 28.25±0.2°.

In some embodiments of the present disclosure, the X-ray powder diffraction spectrum of the above-mentioned A crystal form has characteristic diffraction peaks at the following 2θ angles: 4.69±0.2°, 9.35±0.2°, 10.01±0.2°, 13.28±0.2°, 14.04±0.2°, 16.03±0.2°, 16.83±0.2°, 17.73±0.2°, 18.58±0.2°, 18.74±0.2°, 20.08±0.2°, 21.58±0.2°, 23.53±0.2°, 25.11±0.2°, 25.27±0.2°, 27.80±0.2°, 28.25±0.2°, and 33.00±0.2°.

In some embodiments of the present disclosure, in the X-ray powder diffraction spectrum of the above-mentioned A crystal form, the peak positions and intensities of the characteristic peaks are as shown in Table 1.

TABLE 1

Peak positions and intensities of the characteristic peaks of the X-ray powder diffraction spectrum of the A crystal form

| No. | 2θ angle (°) | Relative intensity (%) | No. | 2θ angle (°) | Relative intensity (%) |
|---|---|---|---|---|---|
| 1 | 4.690 | 100 | 10 | 18.737 | 5.3 |
| 2 | 9.353 | 6.4 | 11 | 20.078 | 6.8 |
| 3 | 10.008 | 3.6 | 12 | 21.580 | 3.7 |
| 4 | 13.276 | 6.9 | 13 | 23.532 | 5.3 |
| 5 | 14.035 | 77.7 | 14 | 25.114 | 3.9 |
| 6 | 16.025 | 7.8 | 15 | 25.269 | 6.3 |
| 7 | 16.831 | 2.4 | 16 | 27.801 | 3.6 |
| 8 | 17.726 | 2.3 | 17 | 28.251 | 7.5 |
| 9 | 18.581 | 1.9 | 18 | 32.999 | 2.1 |

In some embodiments of the present disclosure, the XRPD spectrum of the above-mentioned A crystal form is as shown in FIG. 1, that is, the A crystal form has features represented by the XRPD spectrum as shown in FIG. 1.

In some embodiments of the present disclosure, the analysis data of the XRPD spectrum of the above-mentioned A crystal form is as shown in Table 2.

TABLE 2

XRPD analysis data of the A crystal form

| No. | 2θ angle (°) | Interplanar spacing (Å) | Relative intensity (%) |
|---|---|---|---|
| 1 | 4.690 | 18.8251 | 100 |
| 2 | 9.353 | 9.4476 | 6.4 |
| 3 | 10.008 | 8.8308 | 3.6 |
| 4 | 13.276 | 6.6635 | 6.9 |
| 5 | 14.035 | 6.3049 | 77.7 |
| 6 | 16.025 | 5.5260 | 7.8 |
| 7 | 16.831 | 5.2634 | 2.4 |
| 8 | 17.726 | 4.9995 | 2.3 |
| 9 | 18.581 | 4.7712 | 1.9 |
| 10 | 18.737 | 4.7320 | 5.3 |
| 11 | 20.078 | 4.4189 | 6.8 |
| 12 | 21.580 | 4.1145 | 3.7 |
| 13 | 23.532 | 3.7775 | 5.3 |
| 14 | 25.114 | 3.5430 | 3.9 |
| 15 | 25.269 | 3.5216 | 6.3 |
| 16 | 27.801 | 3.2064 | 3.6 |
| 17 | 28.251 | 3.1562 | 7.5 |
| 18 | 32.999 | 2.7122 | 2.1 |

In some embodiments of the present disclosure, the DSC spectrum of the above-mentioned A crystal form is as shown in FIG. 2, that is, the A crystal form has features represented by the DSC spectrum as shown in FIG. 2.

In some embodiments of the present disclosure, the differential scanning calorimetry curve of the above-mentioned A crystal form has an endothermic peak at 208.18° C.±3° C.

In some embodiments of the present disclosure, the TGA spectrum of the above-mentioned A crystal form is as shown in FIG. 3, that is, the A crystal form has features represented by the TGA spectrum as shown in FIG. 3.

In some embodiments of the present disclosure, the thermogravimetric analysis curve of the above-mentioned A crystal form displays a weight loss of 0.3110±0.2% at 188.49±3° C.

In some embodiments of the present disclosure, in the above-mentioned A crystal form of compound WX_1, x is 1.

The present disclosure also provides a preparation method of the maleate salt of the compound of formula (I), which comprises contacting the compound of formula (I) with maleic acid.

In some embodiments of the present disclosure, the preparation method of the above-mentioned A crystal form of compound WX_1 comprises the following steps:

(1) mixing maleic acid with a solvent;

(2) adding the compound of formula (I) to the mixture of step (1); and (3) filtering and drying;

wherein the solvent is selected from one or more of methanol, ethanol, isopropanol, acetone, and ethyl acetate, and a methanol/water mixed solvent or an isopropanol/water mixed solvent, preferably the methanol/water mixed solvent.

In some embodiments of the present disclosure, the molar ratio of maleic acid to the compound of formula (I) is about 1:1 to 1.1:1.

In some embodiments of the present disclosure, the volume ratio of methanol/water is about 1:1 to 50:1, preferably 1:1 to 20:1; in some specific embodiments of the present disclosure, the volume ratio of methanol/water is about 3:1; and in some specific embodiments of the present disclosure, the volume ratio of methanol/water is about 17:1 to 18:1. In some embodiments of the present disclosure, the volume ratio of isopropanol/water is about 0.5:1 to 5:1, preferably 1:1.

In some embodiments of the present disclosure, step (1) is carried out under heating. In some embodiments of the present disclosure, the heating temperature of step (1) is about 60 to 70° C., preferably about 65° C.

In some embodiments of the present disclosure, in step (2), stirring is carried out after adding the compound of formula (I).

In some embodiments of the present disclosure, in step (2), after adding the compound of formula (I), stirring is carried out under a temperature of about 60 to 70° C., preferably about 65° C.

In some embodiments of the present disclosure, in step (3), cooling is carried out before filtering, and the cooling may be cooling to 20° C.

In some embodiments of the present disclosure, in step (3), stirring may be carried out as necessary after cooling, and the stirring time may be 15 to 22 hours, preferably 18 hours.

In some embodiments of the present disclosure, in step (3), washing is optionally carried out with a solvent prior to drying, and the washing solvent is selected from methanol, ethanol, isopropanol, acetone, or ethyl acetate, and a methanol/water mixed solvent or an isopropanol/water mixed solvent, and is preferably methanol.

The present disclosure also provides a purification method of the above-mentioned A crystal form of compound WX_1, which comprises:

(a) first raising the temperature of a solvent to 45 to 55° C., and then adding the A crystal form of compound WX_1 to the solvent;

(b) stirring at 45 to 55° C. for 1 to 3 hours;

(c) cooling, filtering, and washing the filter cake with a solvent; and (d) drying for 48 to 72 hours;

wherein the solvents described in step (a) and step (c) are each independently selected from one or more of methanol, ethanol, and isopropanol, preferably one of methanol, ethanol or isopropanol, and it is further preferred that the solvents in step (a) and step (c) are both methanol.

In some embodiments of the present disclosure, step (a) is raising the temperature of a solvent to 50° C. and then adding the A crystal form of compound WX_1 to the solvent.

In some embodiments of the present disclosure, step (b) is stirring at 50° C. for 1 to 3 hours.

In some specific embodiments of the present disclosure, step (b) is stirring at 50° C. for 2 hours.

In some embodiments of the present disclosure, the cooling condition in step (c) is cooling to 30° C.

In some specific embodiments of the present disclosure, in step (c), drying is carried out for 64 hours.

The present disclosure also provides a B crystal form of the compound of formula (I), and the X-ray powder diffraction spectrum of the B crystal form has characteristic diffraction peaks at the following 2θ angles: 12.88±0.2°, 14.18±0.2°, 16.72±0.2°, 17.49±0.2°, 19.21±0.2°, 21.06±0.2°, 21.65±0.2°, and 24.14±0.2°.

In some embodiments of the present disclosure, the X-ray powder diffraction spectrum of the above-mentioned B crystal form has characteristic diffraction peaks at the following 2θ angles: 9.86±0.2°, 12.88±0.2°, 14.18±0.2°, 16.72±0.2°, 17.49±0.2°, 19.21±0.2°, 21.06±0.2°, 21.65±0.2°, 24.14±0.2°, 26.29±0.2°, and 27.69±0.2°.

In some embodiments of the present disclosure, the X-ray powder diffraction spectrum of the above-mentioned B crystal form has characteristic diffraction peaks at the following 2θ angles: 9.56±0.2°, 9.86±0.2°, 11.53±0.2°, 12.01±0.2°, 12.88±0.2°, 14.18±0.2°, 15.21±0.2°, 15.66±0.2°, 16.72±0.2°, 17.49±0.2°, 18.79±0.2°, 19.21±0.2°, 19.76±0.2°, 21.06±0.2°, 21.65±0.2°, 22.52±0.2°, 22.93±0.2°, 24.14±0.2°, 24.47±0.2°, 26.29±0.2°, 27.69±0.2°, 28.48±0.2°, 28.79±0.2°, 30.25±0.2°, 30.74±0.2°, 31.67±0.2°, 34.79±0.2°, and 35.18±0.2°.

In some embodiments of the present disclosure, in the X-ray powder diffraction spectrum of the above-mentioned B crystal form, the peak positions and intensities of the characteristic peaks are as shown in Table 3.

TABLE 3

Peak positions and intensities of the characteristic peaks of the X-ray powder diffraction spectrum of the B crystal form

| No. | 2θ angle (°) | Relative intensity (%) | No. | 2θ angle (°) | Relative intensity (%) |
|---|---|---|---|---|---|
| 1 | 9.560 | 13.3 | 16 | 22.516 | 5.2 |
| 2 | 9.857 | 18.8 | 17 | 22.933 | 33.1 |
| 3 | 11.533 | 2.1 | 18 | 24.135 | 100.0 |
| 4 | 12.007 | 10.7 | 19 | 24.471 | 9.6 |
| 5 | 12.876 | 47.8 | 20 | 25.912 | 6.7 |
| 6 | 14.177 | 30.6 | 21 | 26.286 | 41.6 |
| 7 | 15.207 | 3.3 | 22 | 27.685 | 37.6 |
| 8 | 15.659 | 6.2 | 23 | 28.475 | 4.1 |
| 9 | 16.719 | 18.0 | 24 | 28.791 | 2.6 |
| 10 | 17.488 | 34.3 | 25 | 30.250 | 15.9 |
| 11 | 18.792 | 12.9 | 26 | 30.738 | 2.9 |
| 12 | 19.206 | 55.0 | 27 | 31.669 | 15.3 |
| 13 | 19.757 | 2.3 | 28 | 34.786 | 4.1 |
| 14 | 21.060 | 79.9 | 29 | 35.176 | 5.1 |
| 15 | 21.651 | 67.8 | — | — | — |

In some embodiments of the present disclosure, the XRPD spectrum of the above-mentioned B crystal form is as shown in FIG. 4, that is, the B crystal form has features represented by the XRPD spectrum as shown in FIG. 4.

In some embodiments of the present disclosure, the analysis data of the XRPD spectrum of the above-mentioned B crystal form is as shown in Table 4.

TABLE 4

XRPD analysis data of the B crystal form

| No. | 2θ angle (°) | Interplanar spacing (Å) | Relative intensity (%) |
|---|---|---|---|
| 1 | 9.560 | 9.2436 | 13.3 |
| 2 | 9.857 | 8.9655 | 18.8 |
| 3 | 11.533 | 7.6665 | 2.1 |
| 4 | 12.007 | 7.3651 | 10.7 |
| 5 | 12.876 | 6.8696 | 47.8 |
| 6 | 14.177 | 6.2420 | 30.6 |
| 7 | 15.207 | 5.8216 | 3.3 |
| 8 | 15.659 | 5.6546 | 6.2 |
| 9 | 16.719 | 5.2982 | 18.0 |
| 10 | 17.488 | 5.0668 | 34.3 |
| 11 | 18.792 | 4.7181 | 12.9 |
| 12 | 19.206 | 4.6175 | 55.0 |
| 13 | 19.757 | 4.4898 | 2.3 |
| 14 | 21.060 | 4.2149 | 79.9 |
| 15 | 21.651 | 4.1012 | 67.8 |
| 16 | 22.516 | 3.9455 | 5.2 |
| 17 | 22.933 | 3.8747 | 33.1 |

TABLE 4-continued

XRPD analysis data of the B crystal form

| No. | 2θ angle (°) | Interplanar spacing (Å) | Relative intensity (%) |
|---|---|---|---|
| 18 | 24.135 | 3.6845 | 100.0 |
| 19 | 24.471 | 3.6346 | 9.6 |
| 20 | 25.912 | 3.4356 | 6.7 |
| 21 | 26.286 | 3.3876 | 41.6 |
| 22 | 27.685 | 3.2195 | 37.6 |
| 23 | 28.475 | 3.1319 | 4.1 |
| 24 | 28.791 | 3.0983 | 2.6 |
| 25 | 30.250 | 2.9522 | 15.9 |
| 26 | 30.738 | 2.9063 | 2.9 |
| 27 | 31.669 | 2.8230 | 15.3 |
| 28 | 34.786 | 2.5769 | 4.1 |
| 29 | 35.176 | 2.5492 | 5.1 |

In some embodiments of the present disclosure, the DSC spectrum of the above-mentioned B crystal form is as shown in FIG. 5, that is, the B crystal form has features represented by the DSC spectrum as shown in FIG. 5.

In some embodiments of the present disclosure, the differential scanning calorimetry curve of the above-mentioned B crystal form has an endothermic peak at around 225.76° C.

In some embodiments of the present disclosure, the differential scanning calorimetry curve of the above-mentioned B crystal form has an endothermic peak at 225.76° C.±3° C.

In some embodiments of the present disclosure, the TGA spectrum of the above-mentioned B crystal form is as shown in FIG. 6, that is, the B crystal form has features represented by the TGA spectrum as shown in FIG. 6.

In some embodiments of the present disclosure, the thermogravimetric analysis curve of the above-mentioned B crystal form displays weight losses at 52.81° C.±3° C., 184.82° C.±3° C., and 230.03° C.±3° C.

In some embodiments of the present disclosure, the thermogravimetric analysis curve of the above-mentioned B crystal form displays a weight loss of 0.1384% at 52.81° C.±3° C.; an additional weight loss of 0.3565% at 184.82° C.±3° C.; and an additional weight loss of 0.4086% at 230.03° C.±3° C.

In some embodiments of the present disclosure, the thermogravimetric analysis curve of the above-mentioned B crystal form displays a weight loss of 0.1384% at 52.81° C.; an additional weight loss of 0.3565% at 184.82° C.; and an additional weight loss of 0.4086% at 230.03° C.

The present disclosure also provides a preparation method of the above-mentioned B crystal form, which comprises the following steps:

(i) adding the compound of formula (I) into a solvent and heating;
(ii) cooling down slowly, and standing; and
(iii) centrifuging and drying.

In some embodiments, the solvent of step (i) is one or two of ethanol and water, preferably a mixed solvent of ethanol and water.

In some embodiments, the heating temperature in step (i) is 70 to 100° C., preferably 80° C.

In some embodiments, the preparation method of the above-mentioned B crystal form comprises the following steps:

(i) adding the compound of formula (I) into a solvent, and stirring at 70 to 100° C. for 0.5 to 2 hours;
(ii) cooling down slowly, and standing for 8 to 16 hours; and
(iii) centrifuging, and drying for 8 to 16 hours;
wherein the solvent is a mixed solvent of ethanol and water, and the volume ratio of ethanol to water is 3:1.

In some embodiments of the present disclosure, step (i) is adding the compound of formula (I) into a solvent and stirring at 80° C. for 0.5 to 2 hours.

In some specific embodiments of the present disclosure, step (i) is adding the compound of formula (I) into a solvent and stirring at 80° C. for 1 hour.

In another aspect, the present disclosure provides a crystalline composition which comprises the A crystal form of compound WX_1, wherein the weight of the A crystal form of compound WX_1 accounts for 50% or more of the weight of the crystalline composition, preferably 80% or more, more preferably 90% or more, and most preferably 95% or more.

In another aspect, the present disclosure provides a crystalline composition which comprises the B crystal form of the compound of formula (I), wherein the weight of the B crystal form of the compound of formula (I) accounts for 50% or more of the weight of the crystalline composition, preferably 80% or more, more preferably 90% or more, and most preferably 95% or more.

In another aspect, the present disclosure provides a pharmaceutical composition that comprises the maleate salt of the compound of formula (I), the compound of formula (II), compound WX_1, the A crystal form of compound WX_1, the crystalline composition that comprises the A crystal form of compound WX_1, the B crystal form of the compound of formula (I), or the crystalline composition that comprises the B crystal form of the compound of formula (I); and the pharmaceutical composition comprises a therapeutically effective amount of the maleate salt of the compound of formula (I), the compound of formula (II), compound WX_1, the A crystal form of compound WX_1, the crystalline composition that comprises the A crystal form of compound WX_1, the B crystal form of the compound of formula (I), or the crystalline composition that comprises the B crystal form of the compound of formula (I) described in the present disclosure. The pharmaceutical composition of the present disclosure may comprise or may not comprise a pharmaceutically acceptable adjuvant.

In another aspect, the present disclosure also provides the use of the above-mentioned compounds, the A crystal form and the B crystal form in preparation of a drug for treating breast cancer and other cancers.

In another aspect, the present disclosure also provides the use of the maleate salt of the compound of formula (I), the compound of formula (II), compound WX_1, the A crystal form of compound WX_1, the crystalline composition that comprises the A crystal form of compound WX_1, the B crystal form of the compound of formula (I), the crystalline composition that comprises the B crystal form of the compound of formula (I), or a pharmaceutical composition thereof in preparation of a drug for treating a CDK4/6-mediated disease, wherein the disease comprises cancers and is preferably breast cancer or lung cancer.

In another aspect, the present disclosure also provides a method for treating a mammalian (for example, human) disease, wherein the disease is a CDK4/6-mediated disease, and the method comprises administrating a therapeutically effective amount of the maleate salt of the compound of formula (I), the compound of formula (II), compound WX_1, the A crystal form of compound WX_1, the crystalline composition that comprises the A crystal form of compound WX_1, the B crystal form of the compound of formula (I), the crystalline composition that comprises the B crystal form of the compound of formula (I), or a pharmaceutical composition thereof to a mammal (for example, human), wherein the disease comprises cancers and is preferably breast cancer or lung cancer.

In a further aspect, the present disclosure also provides the maleate salt of the compound of formula (I), the compound of formula (II), compound WX_1, the A crystal form of compound WX_1, the crystalline composition that comprises the A crystal form of compound WX_1, the B crystal form of the compound of formula (I), the crystalline composition that comprises the B crystal form of the compound of formula (I), or a pharmaceutical composition thereof for use in treatment of a CDK4/6-mediated mammalian (for example, human) disease, wherein the disease comprises cancers and is preferably breast cancer or lung cancer.

Technical Effects

The maleate salt of the compound of formula (I) has an excellent effect in at least one aspect of bioactivity, safety, and bioavailability. The A crystal form of compound WX_1 and the B crystal form of the compound of formula (I) are very stable, and has low hygroscopicity, good water solubility, and good prospects for formulating into a drug.

Definitions and Explanations

Unless otherwise stated, the following terms and phrases used herein are intended to have the following meanings. A specific phrase or term should not be considered as indefinite or unclear if it is not particularly defined, but should be understood as its ordinary meaning. When a trade name appears herein, it is intended to refer to its corresponding commodity or its active ingredient.

The term "treating" means administering the compound or formulation described in the present application to prevent, ameliorate or eliminate a disease or one or more symptoms associated with the disease, and comprises:

(i) preventing a disease or disease state from occurring in a mammal, particularly when a mammal of this kind is susceptible to the disease state but has not been diagnosed as having the disease state;

(ii) inhibiting a disease or disease state, i.e., restraining its development; and (iii) alleviating a disease or disease state, even if the disease or disease state has subsided.

The term "therapeutically effective amount" means the amount of the compound of the present application that (i) treats or prevents a particular disease, condition or disorder, (ii) alleviates, ameliorates or eliminates one or more symptoms of a particular disease, condition or disorder, or (iii) prevents or delays the onset of one or more symptoms of a particular disease, condition or disorder described herein. The amount of the compound of the present application constituting a "therapeutically effective amount" changes depending on the compound, the state of the disease and its severity, the mode of administration, and the age of the mammal to be treated, but can be routinely determined by those skilled in the art according to their knowledge and the content of the present disclosure.

The term "pharmaceutically acceptable" means that as for those compounds, materials, compositions and/or dosage forms, they are within the scope of reliable medical judgment, suitable for use in contact with human and animal tissues without excessive toxicity, irritation, allergic reactions, other problems or complications, and commensurate with a reasonable benefit/risk ratio.

As a pharmaceutically acceptable salt, for example, a metal salt, an ammonium salt, a salt formed with an organic base, a salt formed with an inorganic acid, a salt formed with an organic acid, a salt formed with an alkaline or acidic amino acid, or the like may be mentioned.

The term "pharmaceutical composition" refers to a mixture comprised of one or more compounds of the present application or a salt thereof with a pharmaceutically acceptable adjuvant. The purpose of the pharmaceutical composition is to facilitate the administration of the compound of the present application to an organism.

The term "pharmaceutically acceptable adjuvant" refers to those adjuvants which have no significant irritating effect on the organism and do not impair the bioactivity and properties of the active compound. Suitable adjuvants are well known to those skilled in the art, such as a carbohydrate, a wax, a water-soluble and/or water-swellable polymer, a hydrophilic or hydrophobic material, gelatin, an oil, a solvent, water, and the like.

The word "comprise" and its variants such as "comprises" or "comprising" should be understood as an open, non-exclusive meaning, i.e., "including but not limited to".

The term "PO" refers to oral administration.

The phrase "QD×3W" refers to once-a-day administration which lasts for 3 weeks.

The pharmaceutical composition of the present application can be prepared by combining the compound of the present application with a suitable pharmaceutically acceptable adjuvant, for example, the pharmaceutical composition may be formulated into a solid, semi-solid, liquid or gaseous preparation such as a tablet, a pill, a capsule, a powder, a granule, an ointment, an emulsion, a suspension, a suppository, an injection, an inhalant, a gel, a microsphere, and an aerosol.

Typical routes of administrating the compound of the present application, the pharmaceutically acceptable salt thereof, or the pharmaceutical composition thereof include, but are not limited to, oral, rectal, topical, inhalation, parenteral, sublingual, intravaginal, intranasal, intraocular, intraperitoneal, intramuscular, subcutaneous, and intravenous administration.

The pharmaceutical composition of the present application can be produced by a method well known in the art, such as a conventional mixing method, a dissolution method, a granulation method, a dragee-making method, a pulverization method, an emulsification method, a freeze-drying method, and the like.

In some embodiments, the pharmaceutical composition is in an oral dosage form. For oral administration, the pharmaceutical composition may be formulated by mixing the active compound with pharmaceutically acceptable adjuvant(s) well known in the art. These adjuvants enable the compound of the present application to be formulated into a tablet, a pill, a lozenge, a dragee, a capsule, a liquid, a gel, a syrup, a suspension, or the like for oral administration to a patient.

The solid composition for oral administration may be prepared by conventional methods of mixing, filling or tableting. For example, it can be obtained by the following method: mixing the active compound with solid adjuvant(s), optionally milling the resulting mixture, adding other suitable adjuvant(s) if necessary, and then processing the mixture into granules to obtain tablets or cores of dragees. Suitable adjuvants include, but are not limited to, a binder, a diluent, a disintegrant, a lubricant, a glidant, a sweetener, a flavoring agent, or the like.

The pharmaceutical composition may also be suitable for being administered parenterally in, for example, a sterile solution, a suspension or a lyophilized product in a suitable unit dosage form.

The intermediate compounds of the present disclosure may be prepared by a variety of synthesis methods well known to those skilled in the art, including the specific embodiments listed below, the embodiments formed by combining the listed embodiments with other chemical synthesis methods, and equivalent alternatives well known to those skilled in the art. Preferred embodiments include, but are not limited to, the Examples of the present disclosure.

The chemical reactions of the specific embodiments of the present disclosure are completed in suitable solvents, and the solvents should be suitable for the chemical changes of the present disclosure and the required reagents and materials. In order to obtain the compound of the present disclosure, it is sometimes necessary for those skilled in the art to modify or select the synthesis steps or reaction schemes based on the existing embodiments.

The present disclosure will be specifically described by way of Examples, however, these Examples are not meant as any limitation to the present disclosure.

All solvents used in the present disclosure are commercially available and may be used without further purification.

The present disclosure adopts the following abbreviations: MW represents microwave; r.t. represents room temperature; aq represents aqueous solution; DCM represents methylene chloride; THF represents tetrahydrofuran; DMSO represents dimethyl sulfoxide; NMP represents N-methylpyrrolidone; EtOAc represents ethyl acetate; EtOH represents ethanol; MeOH represents methanol; dioxane represents dioxane; HOAc represents acetic acid; Boc represents t-butoxycarbonyl, Cbz represents benzyloxycarbonyl, both are amine protecting groups; $Boc_2O$ represents di-tert-butyl dicarbonate; DIPEA represents diisopropylethylamine; TEA or $Et_3N$ represents triethylamine; $BnNH_2$ represents benzylamine; $PMBNH_2$ represents p-methoxybenzylamine; KOAc represents potassium acetate; NaOAc represents sodium acetate; $Cs_2CO_3$ represents cesium carbonate; $K_2CO_3$ represents potassium carbonate; $NaHCO_3$ represents sodium bicarbonate; $Na_2SO_4$ represents sodium sulfate; pyridine represents pyridine; NaOH represents sodium hydroxide; TEA or $Et_3N$ represents triethylamine; NaH represents sodium hydrogen; LiHMDS represents lithium bis(trimethylsilyl)amide; i-PrMgBr represents isopropyl magnesium bromide; t-BuOK represents potassium t-butoxide; t-BuONa represents sodium t-butoxide; $Pd_2$(dba)3 represents tris(dibenzylideneacetone)dipalladium; $Pd(PPh_3)_4$ represents tetrakis(triphenylphosphine)palladium; $Pd(dppf)Cl_2.CH_2Cl_2$ represents [1,1'-bis(diphenylphosphino)ferrocene]palladium dichloride.dichloromethane; $Pd(OAc)_2$ represents palladium acetate; $Pd(PPh_3)_2Cl_2$ represents di(triphenylphosphino)palladium dichloride; $Rh(PPh_3)_3Cl$ represents tris(triphenylphosphino) rhodium chloride; $Pd(OH)_2$ represents palladium hydroxide; Xantphos represents 4,5-bis(diphenylphosphino)-9,9-dimethylxanthene; Xphos represents 2-dicyclohexylphosphino-2',4',6'-triisopropylbiphenyl; BINAP represents (±)-2,2'-bis-(diphenylphosphino)-1,1'-binaphthyl; Xantphos represents 4,5-bis-(diphenylphosphino)-9,9-dimethylxanthene; Xphos-Pd-G1 represents chloro(2-dicyclohexylphosphino-2',4',6'-triisopropyl-1,1'-biphenyl)[2-(2'-aminoethylphenyl)]palladium(II); Xphos-PD-$G_2$ represents chloro(2-dicyclohexylphosphino-2',4',6'-triisopropyl-1,1'-biphenyl) [2-(2'-amino-1,1'-biphenyl]palladium(II); Xphos-Pd-$G_3$ represents mesylate (2-dicyclohexylphosphino-2',4',6'-triisopropyl-1,1'-biphenyl)[2-(2'-amino-1,1'-biphenyl)]palladium(II); 12 represents elementary iodide; LiCl represents lithium chloride; HCl represents hydrochloric acid; maleic acid represents maleic acid.

The compounds are named manually or by ChemDraw® software, and the commercial compounds adopt the names listed under the catalogues of the suppliers.

Powder X-Ray Diffraction (Also Referred to as "X-Ray Powder Diffraction", X-Ray Powder Diffractometer, XRPD) Method of the Present Disclosure Model of instrument: Bruker D8 advance X-ray diffractometer Test method: About 10 to 20 mg of a sample is used for XRPD detection.

Detailed parameters of XRPD are as follows:

Light pipe: Cu, kα, (λ=1.54056 Å).

Voltage of light pipe: 40 kV, current of light pipe: 40 mA

Divergence slit: 0.60 mm

Detector slit: 10.50 mm

Anti-scatter slit: 7.10 mm

Scan range: 4 to 40 deg

Step size: 0.02 deg

Step length: 0.12 seconds

Rotation speed of sample pan: 15 rpm

It should be noted that in an X-ray powder diffraction spectrum (XRPD), the diffraction spectrum obtained from a crystalline compound is often characteristic for a specific crystal, wherein the relative intensity of a spectral band (especially at a low angle) may vary due to the dominant orientation effects generated by the differences in crystallization conditions, particle sizes and other measurement conditions. Therefore, the relative intensities of the diffraction peaks are not characteristic for the targeted crystal. When judging whether a crystal is the same with a known crystal, the relative positions of the peaks rather than the relative intensities should be paid more attention. Furthermore, as for any given crystal, there may be slight errors in the peak positions, which is also well known in the field of crystallography. For example, the peak positions may be shifted due to a change in temperature or a sample movement during the analysis of a sample, a calibration of the instrument, or the like. The measurement error of the 2θ value is about ±0.2° sometimes. Therefore, this error should be taken into account when determining the structure of each crystal. In an XRPD spectrum, the peak position is usually expressed by the 2θ angle or the interplanar distance d, and there is a simple conversion relationship between them: d=λ/2 sin θ, wherein d represents the interplanar distance (also called "interplanar spacing"), λ represents the wavelength of the incident X-ray, and θ is the diffraction angle. As for the same kind of crystal of the same compound, the peak positions of the XRPD spectrum thereof have similarities on the whole, and the errors of the relative intensities may be relatively large. It should also be noted that in the identification of a mixture, some of the diffraction lines are missing due to factors such as a decrease in content. At this time, there is no need to rely on all the spectral bands observed in a high-purity sample, and even one spectral band may be characteristic for a given crystal.

Differential Thermal Analysis (Also Referred to as "Differential Scanning Calorimetry", Differential Scanning Calorimeter, DSC) Method of the Present Disclosure Model of instrument: TA Q2000 differential scanning calorimeter Test method: A sample (about 1 mg) is taken and placed in a DSC aluminum pan for testing. The sample is heated from 25° C. to 300° C. at a heating rate of 10° C./min under the condition of 50 mL/min of $N_2$.

DSC measures the transition temperature when a crystal absorbs or releases heat due to the changes in its crystal structure or the melting of the crystal. As for the same kind of crystal of the same compound, in continuous analyses, the errors of the thermal transition temperature and the melting point are typically within about 5° C., usually within about 3° C. When we say a compound has a given DSC peak or melting point, this means that the DSC peak ±5° C. or the melting point ±5° C. DSC provides an auxiliary method for identifying different crystals. Different crystalline forms may be identified based on the characteristics of their different transition temperatures. It should be noted that, as for a mixture, the DSC peak or melting point thereof may vary over a larger range. In addition, the melting temperature is related to the heating rate since there is a decomposition during the melting of a substance.

Thermogravimetric Analysis (Thermal Gravimetric Analyzer, TGA) Method of the Present Disclosure Model of instrument: TA Q5000IR thermal gravimetric analyzer Test method: A sample (2 to 5 mg) is taken and placed in a TGA platinum pan for testing. The sample is heated from the room temperature to 350° C. at a heating rate of 10° C./min under the condition of 25 mL/min of $N_2$.

DETAILED DESCRIPTION

Figure 1:
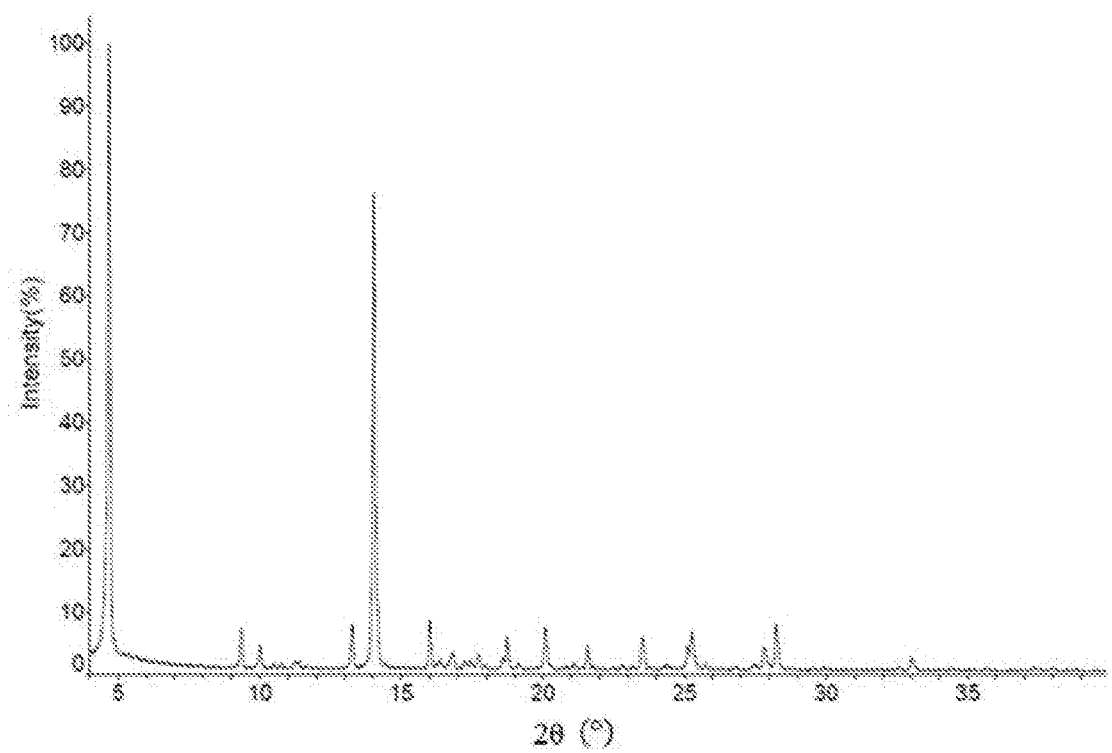
FIG. 1 is an XRPD spectrum of Cu—Kα radiation of the A crystal form of compound WX_1.
Figure 2:
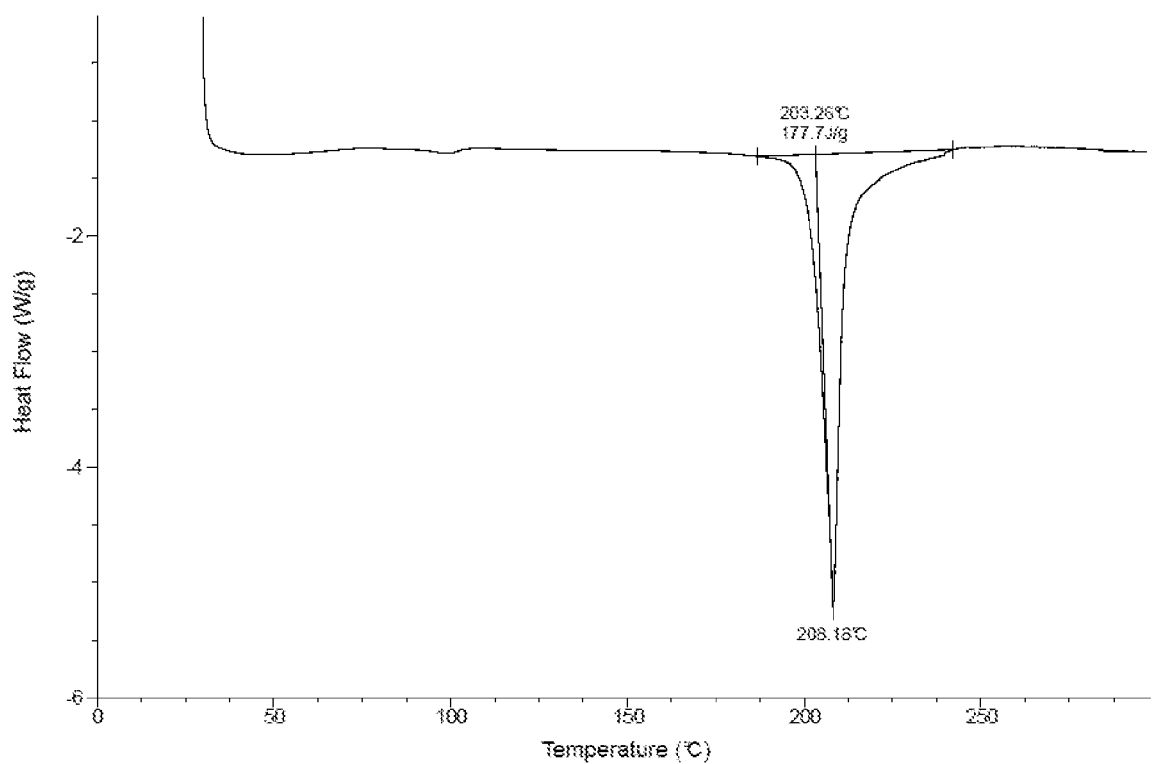
FIG. 2 is a DSC spectrum of the A crystal form of compound WX_1.
Figure 3:
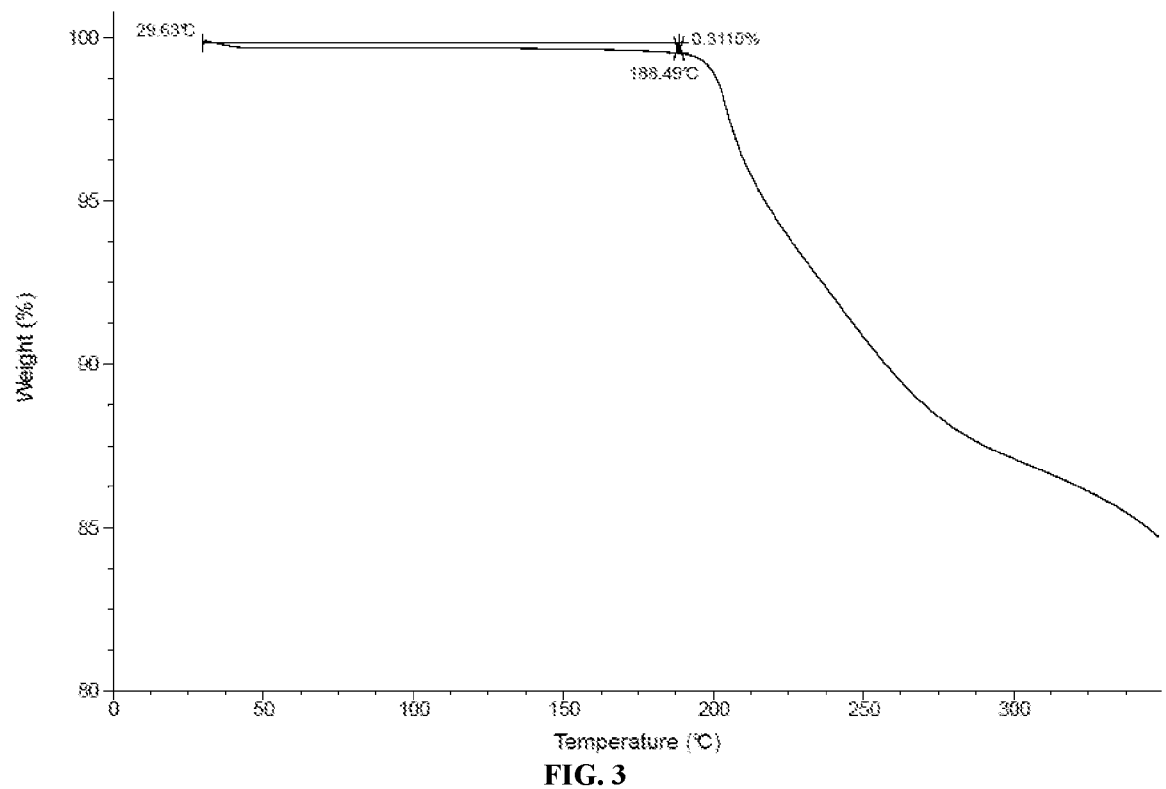
FIG. 3 is a TGA spectrum of the A crystal form of compound WX_1.
Figure 4:
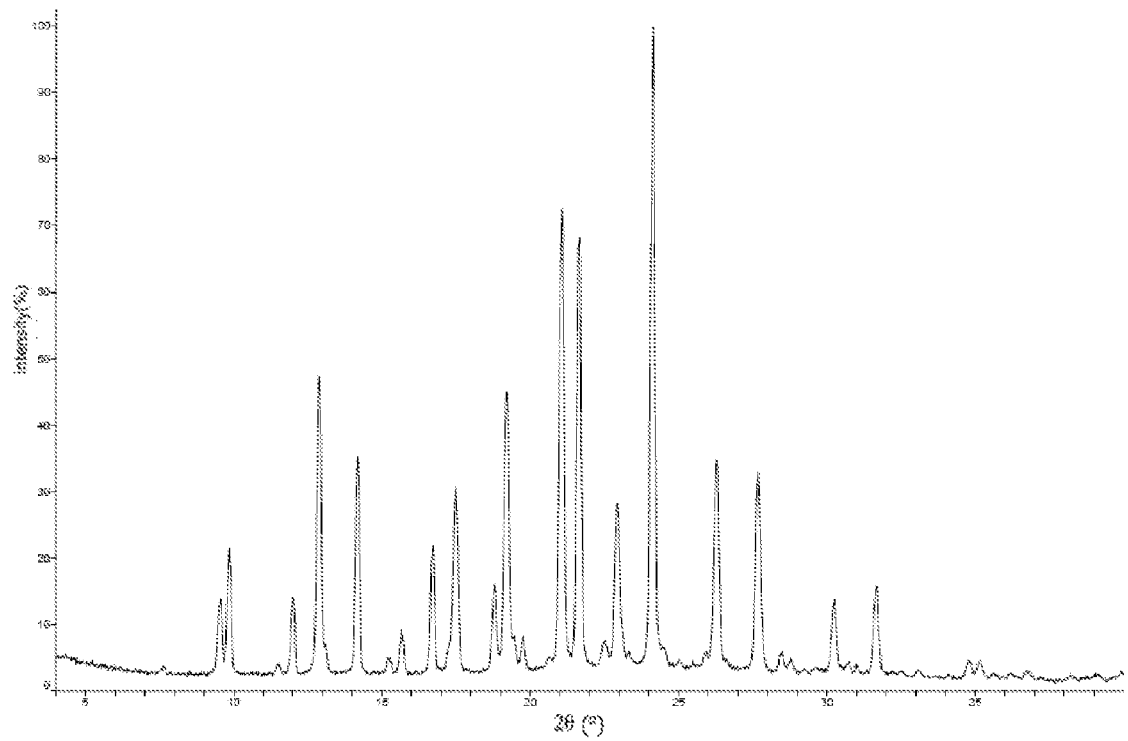
FIG. 4 is an XRPD spectrum of Cu—Kα radiation of the B crystal form of the compound of formula (I).
Figure 5:
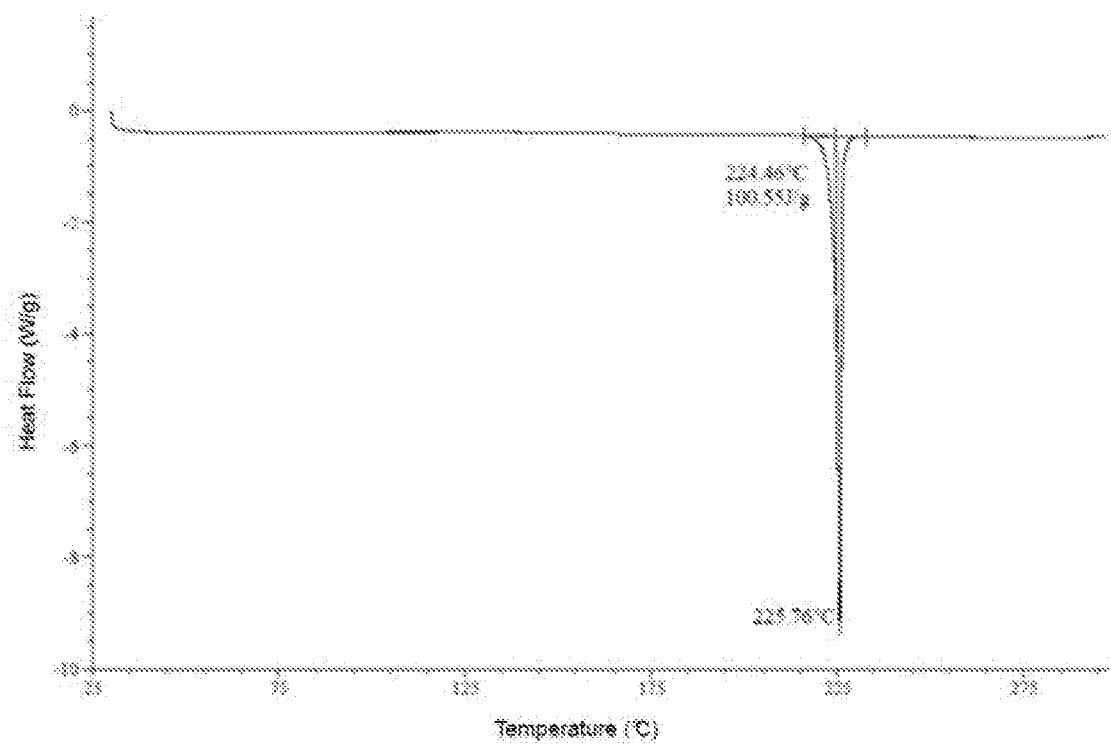
FIG. 5 is a DSC spectrum of the B crystal form of the compound of formula (I).
Figure 6:
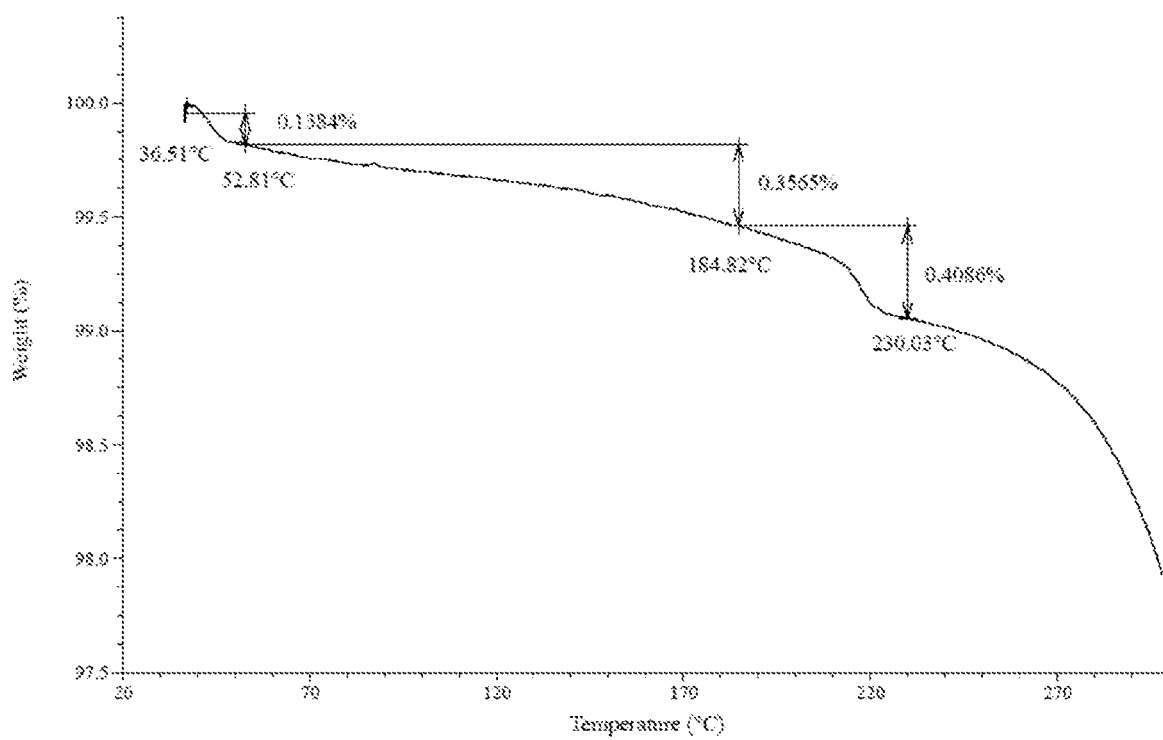
FIG. 6 is a TGA spectrum of the B crystal form of the compound of formula (I).

In order to better understand the contents of the present disclosure, the present disclosure will be further described in conjunction with the specific examples, but the specific embodiments are not limitations to the content of the present disclosure.

Preparation of the A crystal form of WX_1

Maleic acid (439.30 g, 99.6% purity), methanol (11.90 L) and water (666.00 mL) were added to a 50 L reaction kettle at 20° C., and the resulting mixture was heated to 65° C., and then the compound of formula (I) (1.66 kg) was added to the reaction kettle. After the reaction mixture was stirred at 65° C. for 1 hour, the mixture was cooled to 20° C. and stirred for 18 hours. The obtained mixture was filtered, and the filter cake was dried under vacuum at 45° C. for 70 hours after being washed with methanol (2 L×2) to obtain a crude product of the A crystal form of compound WX_1 (1.55 kg, 98.88% purity). $^1$H NMR (400 MHz, DMSO-$d_6$) δ 9.88 (s, 1H), 8.67 (s, 1H), 8.61 (d, J=3.9 Hz, 1H), 8.17 (d, J=9.2 Hz, 1H), 8.11 (d, J=2.9 Hz, 1H), 7.93 (d, J=9.3 Hz, 1H), 7.67 (d, J=9.0 Hz, 1H), 7.49 (dd, J=9.1, 3.1 Hz, 1H), 6.05 (s, 2H), 4.15 (s, 3H), 3.60 (td, J=14.0, 7.0 Hz, 1H), 3.33 (br d, J=6.0 Hz, 4H), 3.29 (br d, J=5.9 Hz, 4H), 1.51 (d, J=6.9 Hz, 6H).

Methanol (8.65 L) was added to a 10 L three-necked flask at 30° C., the solution was heated to 50° C., and then the crude product of the A crystal form of WX_1 (865.00 g, 1.52 mol, 1.00 eq) was added into the reaction flask. The reaction mixture was stirred for 2 hours at 50° C. Then, the reaction mixture was cooled to 30° C., filtered, and the filter cake was dried under vacuum at 45° C. for 64 hours after being washed with methanol (1 L×2) to obtain the A crystal form of WX_1 (780.00 g, 98.98% purity). $^1$H NMR (400 MHz, DMSO-$d_6$) δ 9.83 (s, 1H), 8.67 (s, 1H), 8.60 (d, J=4.0 Hz, 1H), 8.16 (d, J=9.0 Hz, 1H), 8.10 (d, J=2.9 Hz, 1H), 7.93 (d, J=9.2 Hz, 1H), 7.67 (d, J=9.0 Hz, 1H), 7.49 (dd, J=9.2, 3.0 Hz, 1H), 6.04 (s, 2H), 4.15 (s, 3H), 3.60 (td, J=14.0, 7.0 Hz, 1H), 3.34 (br d, J=3.5 Hz, 4H), 3.29 (br d, J=5.8 Hz, 4H), 1.51 (d, J=7.0 Hz, 6H)

Preparation of the Compound of Formula (I)

Preparation Scheme 1:

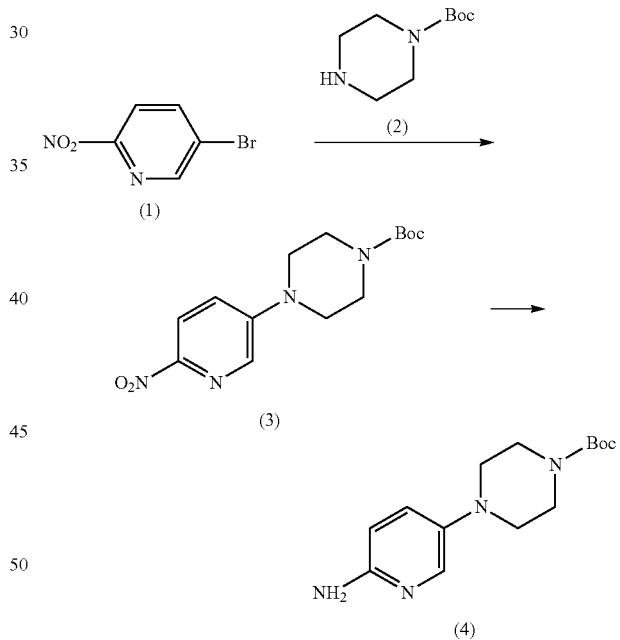

Step 1:

To a solution of compound (1) (20.00 g, 98.53 mmol, 1.00 eq) in dimethyl sulfoxide (52 mL), compound (2) (24.00 g, 128.86 mmol, 1.31 eq) and triethylamine (20.00 g, 197.65 mmol, 2.01 eq) were added. The solution was heated to 60° C. and stirred for 18 hours. TLC (petroleum ether:ethyl acetate=3:1) showed the completion of the reaction. The solution was diluted with water (200 mL), stirred for 30 minutes, and then filtered. The filter cake was washed with water and dried under vacuum to obtain a crude product. The crude product was purified by a silica gel column (petroleum ether:ethyl acetate=50:1 to 20:1) to obtain compound (3) (27.00 g, 87.57 mmol, yield: 88.87%). $^1$H NMR (400 MHz, CDCl₃) δ8.18 (d, J=9.03 Hz, 1H), 8.13 (d, J=2.89 Hz, 1H), 7.21 (dd, J=9.10, 2.95 Hz, 1H), 3.69-3.59 (m, 4H), 3.51-3.40 (m, 4H), 1.49 (s, 9H).

Step 2:

Under the protection of nitrogen gas, to a solution of compound (3) (28.00 g, 90.81 mmol, 1.00 eq) in methanol (600 mL), palladium on carbon (6%, 1.7 g) was added. The suspension was evacuated and charged with hydrogen gas for several times. The solution was stirred for 18 hours at 50° C. under an atmosphere of hydrogen gas (50 psi). TLC (dichloromethane:methanol=10:1) showed that the starting materials were completely reacted. The suspension was filtered, and the filtrate was dried by rotary evaporation to obtain compound (4) (24.13 g, 86.69 mmol, yield: 95.46%). ¹H NMR (400 MHz, CDCl₃) δ 7.78 (d, J=2.64 Hz, 1H) 7.18 (dd, J=8.78, 2.89 Hz, 1H) 6.50 (d, J=8.78 Hz, 1H) 4.21 (br s, 2H) 3.60-3.54 (m, 4H) 3.00-2.92 (m, 4H) 1.48 (s, 9H).

Preparation Scheme 2:

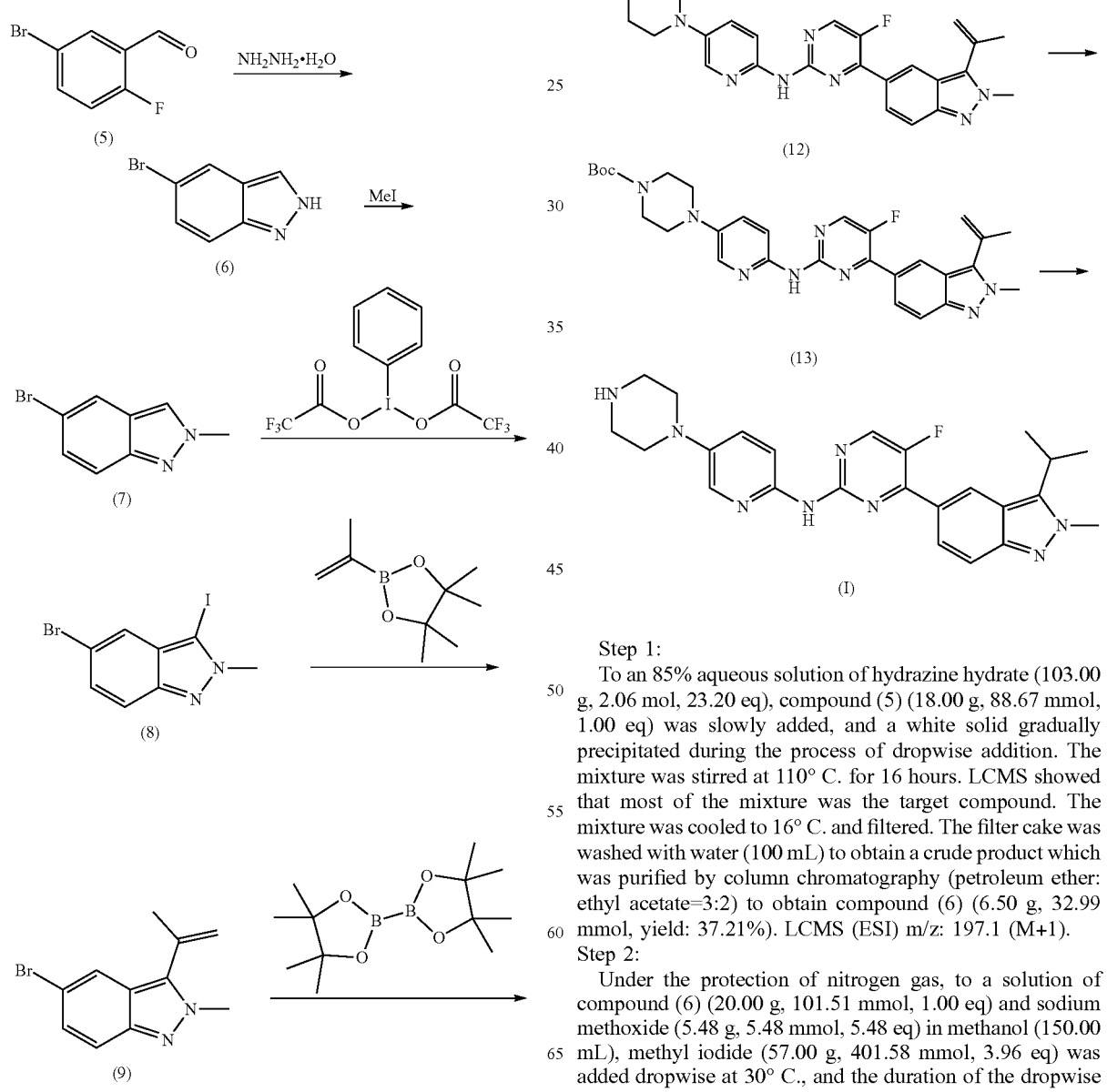

Step 1:

To an 85% aqueous solution of hydrazine hydrate (103.00 g, 2.06 mol, 23.20 eq), compound (5) (18.00 g, 88.67 mmol, 1.00 eq) was slowly added, and a white solid gradually precipitated during the process of dropwise addition. The mixture was stirred at 110° C. for 16 hours. LCMS showed that most of the mixture was the target compound. The mixture was cooled to 16° C. and filtered. The filter cake was washed with water (100 mL) to obtain a crude product which was purified by column chromatography (petroleum ether:ethyl acetate=3:2) to obtain compound (6) (6.50 g, 32.99 mmol, yield: 37.21%). LCMS (ESI) m/z: 197.1 (M+1).

Step 2:

Under the protection of nitrogen gas, to a solution of compound (6) (20.00 g, 101.51 mmol, 1.00 eq) and sodium methoxide (5.48 g, 5.48 mmol, 5.48 eq) in methanol (150.00 mL), methyl iodide (57.00 g, 401.58 mmol, 3.96 eq) was added dropwise at 30° C., and the duration of the dropwise addition was controlled to 1 hour. The mixture was then heated to 85° C. and stirred for 5 hours. LCMS showed that the starting materials were almost completely consumed and the MS of the desired compound was detected. The mixture was cooled to 16° C. and concentrated to obtain a crude product. The crude product was diluted with a 3% aqueous solution of NaHCO$_3$ (30 mL) and extracted with ethyl acetate (80 mL×2). The organic phase was concentrated under reduced pressure. The residue was purified by column chromatography (petroleum ether:ethyl acetate=30:1 to 1:1) to obtain compound (7) (8.40 g, 39.80 mmol, yield: 39.21%). $^1$H NMR (400 MHz, DMSO-d$_6$) δ8.33 (s, 1H), 7.95 (s, 1H), 7.58 (d, J=8.0 Hz, 1H), 7.30 (dd, J=1.8 Hz, 8 Hz, 1H), 4.18 (s, 1H). LCMS (ESI) m/z: 210.8 (M+1).

Step 3:

To a solution of compound (7) (8.40 g, 39.80 mmol, 1.00 eq) in dichloromethane (90 mL), pyridine (4.72 g, 59.70 mmol, 1.5 eq) and bis(trifluoroacetoxy)iodobenzene (20.54 g, 47.76 mmol, 1.20 eq) were added at 30° C. The mixture was stirred for 0.5 hours, then iodine (12.12 g, 47.76 mmol, 1.20 eq) was added and stirring was continued for 23.5 hours. LCMS showed that the reaction was complete. The mixture was filtered to obtain compound (8) (8.20 g, crude product). LCMS (ESI) m/z: 336.9 (M+1).

Step 4:

Under the protection of nitrogen gas, to a solution of compound (8) (7.68 g, 22.79 mmol, 1.00 eq) and isopropenyl borate (4.21 g, 25.07 mmol, 1.11 eq) in dioxane (90.00 mL), a saturated aqueous solution (30 mL) of K$_2$CO$_3$ (9.45 g, 68.38 mmol, 3.00 eq) and Pd(dppf)Cl$_2$·CH$_2$Cl$_2$ (1.86 g, 2.28 mmol, 0.10 eq) were added. The mixture was stirred at 100° C. for 3 hours. TLC showed that the starting materials were almost completely reacted. The mixture was cooled to 30° C., filtered, and the filtrate was extracted with ethyl acetate (100 mL×3), washed with water (50 mL×3), washed with saturated brine (20 mL×3), dried over anhydrous Na$_2$SO$_4$, filtered, and concentrated. The residue was purified by column chromatography (petroleum ether:ethyl acetate=1:1) to obtain compound (9) (5.36 g, 21.34 mmol, yield: 93.66%).

Step 5:

Under the protection of nitrogen gas, to a solution of compound (9) (2.80 g, 11.15 mmol, 1.00 eq) and bis(pinacolato)diboron (3.40 g, 13.38 mmol, 1.20 eq) in dioxane (56.00 mL), KOAc (3.28 g, 33.45 mmol, 3.00 eq) and Pd(dppf)Cl$_2$·CH$_2$Cl$_2$ (1.82 g, 2.23 mmol, 0.20 eq) were added. The mixture was stirred at 100° C. for 5 hours. LCMS showed that the reaction was complete and the MS of the target compound was detected. The mixture was cooled to 16° C. and the mixture was diluted with ethyl acetate (20 mL), and filtered to obtain a filtrate. The filtrate was purified by column chromatography (petroleum ether:ethyl acetate=1:1) to obtain compound (10) (3.30 g, 9.96 mmol, yield: 89.33%, purity 90%). LCMS (ESI) m/z: 299.1 (M+1).

Step 6:

Under the protection of nitrogen gas, to a solution of 2,4-dichloro-5-fluoro-pyrimidine (147.83 mg, 885.34 µmol, 1.20 eq) and compound (10) (220.00 mg, 737.78 µmol, 1.00 eq) in dioxane (4 mL), K$_2$CO$_3$ (305.91 mg, 2.21 mmol, 3.00 eq) and Pd(dppf)Cl$_2$CH$_2$Cl$_2$ (120.50 mg, 147.56 µmol, 0.20 eq) were added. The mixture was stirred at 100° C. for 3.5 hours. TLC showed that most of the starting materials were completely reacted, and LCMS showed that the majority was the MS of the target compound. The mixture was cooled to 30° C. and filtered. The filter cake was washed with ethyl acetate (5 mL) and the filtrate was concentrated. The residue was purified by column chromatography (petroleum ether: ethyl acetate=1:0 to 6:1) to obtain compound (11) (210.0 mg, 693.69 µmol, yield: 94.02%). LCMS (ESI) m/z: 303.0 (M+1).

Step 7:

To a solution of compound (11) (200.00 mg, 660.65 µmol, 1.00 eq) in dioxane (10.00 mL), compound (4) (220.67 mg, 792.79 µmol, 1.20 eq), Pd$_2$(dba)$_3$ (60.50 mg, 66.07 µmol, 0.10 eq) and Xantphos (76.45 mg, 132.13 µmol, 0.20 eq) and cesium carbonate (430.51 mg, 1.32 mmol, 2.00 eq) were added. The solution was heated to 110° C. under the protection of nitrogen gas and stirred for 16 hours. LCMS showed that the reaction was complete. The solution was cooled to 25° C., filtered and concentrated to obtain a crude product. The crude product was purified by preparative TLC (ethyl acetate:petroleum ether=1:2) to obtain compound (12) (320.00 mg, 587.57 µmol, yield: 88.94%). LCMS (ESI) m/z: 545.3 (M+1).

Step 8:

Under the protection of nitrogen gas, to a solution of compound (12) (320.00 mg, 587.57 µmol, 1.00 eq) in methanol (20.00 mL), palladium on carbon (200.00 mg) and acetic acid (2.10 g, 34.97 mmol, 59.52 eq) were added. The suspension was evacuated and charged with hydrogen gas for several times. The solution was stirred at 50° C. under an atmosphere of hydrogen gas (32 psi) for 96 hours. LCMS showed that the reaction was complete. The suspension was cooled to 25° C., filtered and concentrated to obtain compound (13) (500.00 mg, crude product). LCMS (ESI) m/z: 547.1 (M+1).

Step 9:

To a solution of compound (13) (10.00 g, 18.29 mmol, 1.00 eq) in dichloromethane (80.00 mL), HCl/EtOAc (4 mol/L, 80.00 ml, 17.50 eq) was added and stirred for 2 hours at 20° C. LCMS showed that the reaction was complete. The reaction mixture was filtered, and the filter cake was washed with ethyl acetate (50 mL×3). The filter cake was dissolved in deionized water (100 mL), the pH was adjusted to 7 to 8 with a saturated aqueous sodium hydrogen carbonate solution, and the system was extracted with dichloromethane (200 mL×3). The combined organic phases were washed with saturated brine (100 mL), dried over anhydrous sodium sulfate, and concentrated. The obtained crude product was stirred with tert-butanol (50 mL) at 80° C. for 1 hour. The system was cooled to 20° C. and filtered. The filter cake was washed with methanol (30 mL×2) and dried to obtain the compound of formula (I) (7.50 g, 16.63 mmol, yield: 90.92%, purity: 99%). 1H NMR (400 MHz, Methanol-d4) δ8.72 (s, 1H), 8.42 (d, J=4.1 Hz, 1H), 8.22 (d, J=9.0 Hz, 1H), 8.04 (d, J=9.3 Hz, 1H), 8.01 (d, J=2.9 Hz, 1H), 7.63 (d, J=9.2 Hz, 1H), 7.45 (dd, J=9.2, 3.0 Hz, 1H), 4.18 (s, 3H), 3.63 (quin, J=7.0 Hz, 1H), 3.12 (dd, J=6.1, 3.8 Hz, 4H), 3.02-2.97 (m, 4H), 1.59 (d, J=7.0 Hz, 6H). LCMS (ESI) m/z: 447.1 (M+1).

Preparation of the B Crystal Form of the Compound of Formula (I)

About 90 mg of the compound of formula (I) was placed in a 1.5 mL glass vial, and about 1.2 mL of a mixed solvent (EtOH:H$_2$O$_2$O=3:1) was added. The resulting suspension was stirred at 80° C. for 1 hour, and the heating was turned off. The mixture was cooled down slowly and left to stand overnight. The suspension was centrifuged rapidly (14000 rpm, 5 min), and the obtained solid was further dried in a vacuum oven at 40° C. overnight to obtain the B crystal form of the compound of formula (I).

Preparation of the Compound of Formula (a)

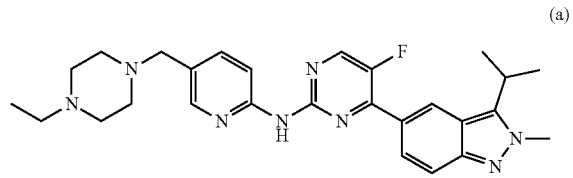 [SMILES: CCN1CCN(Cc2ccc(Nc3ncc(F)c(-c4ccc5nn(C)c(C(C)C)c5c4)n3)nc2)CC1]

Step 1

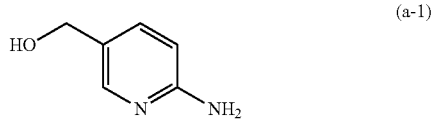

Under the protection of nitrogen gas, a solution of methyl 6-aminopyridine-3-formate (5.00 g) in tetrahydrofuran (50 mL) was added to a solution of LiAlH₄ (1.5 g) in tetrahydrofuran (100 mL), and the mixture was stirred at 70° C. for 16 hours. TLC showed that the reaction was complete. The mixture was cooled to 20° C. Water (1.5 mL), an aqueous solution of sodium hydroxide (15%, 1.5 mL) and water (4.5 mL) were added sequentially and stirred for 0.5 hours. The mixture was filtered. The filtrate was concentrated to give a yellow solid, which was washed with (petroleum ether:ethyl acetate=1:10). The residual yellow solid was the compound of formula (a-1) (2.6 g).
Step 2

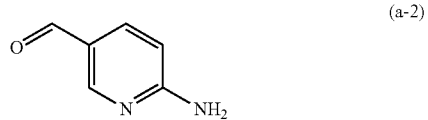

Manganese dioxide (17.51 g) was added to a solution of the compound of formula (a-1) in dichloromethane (30 mL), and the mixture was stirred at 50° C. for 16 hours. TLC (petroleum ether:ethyl acetate=1:1) showed that the reaction was complete. The mixture was cooled to 20° C. and filtered, and the filtrate was concentrated to obtain the compound of formula (a-2) (2.10 g) as a yellow solid. The compound of formula (a-2) was directly used in the next step without purification.
Step 3

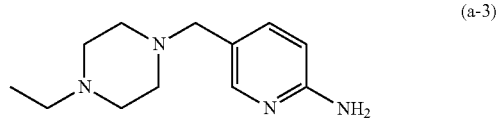 [SMILES: CCN1CCN(Cc2ccc(N)nc2)CC1]

1-ethylpiperazine (1.87 g) was added to a solution of the compound of formula (a-2) (2.00 g) in methanol (20 mL), and the mixture was stirred at 20° C. for 1 hour. Then NaBH₃CN (sodium cyanoborohydride, 2.57 g) was added, and the mixture was stirred at 20° C. for 15 hours. LCMS showed that the reaction was complete. The solvent was removed by concentration under reduced pressure. The residue was purified by preparative HPLC (basic) to obtain the compound of formula (a-3) (800 mg) as a yellow solid. ¹H NMR (400 MHz, CDCl₃) δ 7.97 (d, J=2.0 Hz, 1H), 7.42 (dd, J=8.3, 2.3 Hz, 1H), 6.48 (d, J=8.4 Hz, 1H), 4.38 (br. s, 2H), 3.38 (s, 2H), 2.61-2.31 (m, 10H), 1.08 (t, J=7.2 Hz, 3H).
Step 4

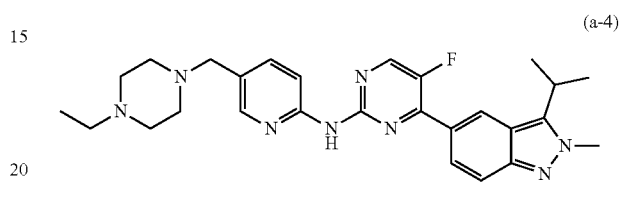

Under the protection of nitrogen gas, Pd₂(dba)3 (151.24 mg), Xantphos (191.13 mg) and Cs₂CO₃ (538.14 mg) were added to a solution of compound (11) (250.00 mg) and the compound of formula (a-3) (200.13 mg) in dioxane (8 mL). The mixture was stirred at 100° C. for 16 hours, and the color of the mixture turned brown. TLC and LCMS showed that the starting materials were completely reacted. The mixture was cooled to 20° C., diluted with ethyl acetate (20 mL), and filtered. The filter cake was washed with ethyl acetate (4 mL), and the filtrate was concentrated to obtain a crude product. Methanol (8 mL) was added to the crude product and the mixture was left to stand for 2 hours at 30° C., and a yellow precipitate was precipitated and filtered. The filter cake was washed with methanol (2 mL), and dried to obtain the compound of formula (a-4) (143.00 mg). ¹H NMR (400 MHz, Methanol-d₄) δ9.99 (s, 1H), 8.65 (s, 1H), 8.64 (s, 1H), 8.21 (t, J=8.8 Hz, 2H), 8.00 (d, J=9.2 Hz, 1H), 7.74 (d, J=9.2 Hz, 1H), 7.67 (d, J=8.8 Hz, 1H), 5.73 (s, 1H), 5.44 (s, 1H), 4.17 (s, 3H), 3.43 (s, 2H), 2.38-2.27 (m, 13H), 0.97 (t, J=6.8 Hz, 3H). LCMS (ESI) m/z: 487.2 (M+1).
Step 5

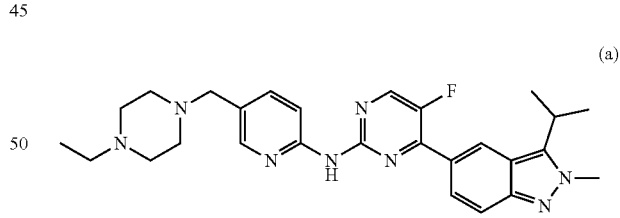

The compound of formula (a-4) (120.00 mg) was added to a solution of Pd/C (20 mg) in methanol (5 mL). Hydrogen gas was introduced into the system and the pressure was maintained at 15 Psi. The mixture was stirred at 50° C. for 16 hours. LCMS showed that the reaction was complete. The mixture was filtered and the filtrate was concentrated. The residue was purified by preparative HPLC (HCl) to obtain the compound of formula (a) (68.00 mg). ¹H NMR (400 MHz, Methanol-d₄) δ9.99 (s, 1H), 8.72 (s, 1H), 8.65 (s, 1H), 8.25 (d, J=8.0 Hz, 1H), 8.19 (s, 1H), 7.94 (d, J=4.8 Hz, 1H), 7.67 (d, J=8.8 Hz, 2H), 4.16 (s, 3H), 3.62 (t, J=6.8 Hz, 1H), 3.44 (s, 2H), 2.55-2.31 (m, 10H), 1.51 (d, J=6.4 Hz, 6H), 0.98 (s, 3H). LCMS (ESI) m/z: 489.3 (M+1).

Study on the Hygroscopicity of the A Crystal Form of Compound WX_1

Experimental Conditions:

Model of instrument: SMSDVS Advantage dynamic vapor sorption analyzer

Test conditions: A sample (10 to 15 mg) was placed in a DVS sample pan for testing.

DVS parameters:

Temperature: 25° C.

Balance: dm/dt=0.01%/min (minimum: 10 min, maximum: 180 min)

Drying: drying for 120 min at 0% RH

Test gradient of RH (%): 10%

Test gradient range of RH (%): 0%-90%-0%

Evaluation Criteria of Hygroscopicity:

| Classification of hygroscopicity | Hygroscopic weight gain *($\Delta$ W %) |
|---|---|
| deliquescent | absorb sufficient amount of water to form a liquid |
| highly hygroscopic | $\Delta$ W % $\geqslant$ 15% |
| hygroscopic | 15% > $\Delta$ W % $\geqslant$ 2% |
| slightly hygroscopic | 2% > $\Delta$ W % $\geqslant$ 0.2% |
| non-hygroscopic or almost non-hygroscopic | $\Delta$ W % < 0.2% |

*Hygroscopic weight gain at 25 ± 1° C. and 80 ± 2% RH

Experimental results: The hygroscopic weight gain of the A crystal form of compound WX_1 at 25° C. and 80% RH was 1.48%.

Experimental conclusion: The A crystal form of compound WX_1 is slightly hygroscopic.

Study on the Polymorphs of Compound WX_1

The A crystal form of compound WX_1 was heated and then dissolved in a corresponding solvent, and stirred at 40° C. in the dark for 2 days. The solution was centrifuged to obtain a precipitate, which was dried and then subjected to an XRPD detection. The results were as follows:

| No. | Solvent | Crystal form |
|---|---|---|
| 1 | methanol | A crystal form |
| 2 | ethanol | A crystal form |
| 3 | isopropanol | A crystal form |
| 4 | acetone | A crystal form |
| 5 | ethyl acetate | A crystal form |
| 6 | methanol-water (3:1) | A crystal form |
| 7 | ethanol-water (3:1) | amorphous (Volatilization) |
| 8 | acetone-water (1:2) | amorphous (Volatilization) |
| 9 | isopropanol-water (1:1) | A crystal form (Volatilization) |

Notes: Volatilization referred to heating and then dissolving the A crystal form of compound WX_1 in a corresponding solvent, centrifuging, taking the supernatant for volatilization, and subjecting the precipitated crystal to an XRPD detection.

Solubility Tests of the Compound of Formula (I) and the A Crystal Form of Compound WX_1

Samples (about 2 mg) (if the sample was a salt, the required amount of the salt was calculated according to the salt factor in accordance with the criterion that the compound of formula (I) was 2 mg) were weighed respectively and added to a 1.5 mL glass vial. Different vehicles (1 mL) were then added respectively. The above-mentioned suspension was placed on a magnetic stirrer for stirring (room temperature 25 to 27° C.). After stirring for 24 hours, samples were taken. The samples were first centrifuged, and the supernatants were taken. After appropriate dilution according to the situation of the dissolution, the concentrations were determined by HPLC. The results were as follows:

| | Solubility | | | |
|---|---|---|---|---|
| Sample | $H_2O$ (mg/mL) | SGF (mg/mL) | FaSSIF (mg/mL) | FeSSIF (mg/mL) |
| compound of formula (I) | 0.01 | >2.0 | 0.013 | 1.60 |
| A crystal form of compound WX_1 | 1.14 | >2.0 | 0.023 | 1.60 |

Notes:

FaSSIF: to simulate the intestinal fluid in the small intestine of human in a hunger state before meal;

FeSSIF: to simulate the intestinal fluid in the small intestine of human in a full state after meal;

SGF: to simulate the gastric juice in the empty stomach of human in a hunger state As might be seen from the above table, the solubility of the A crystal form of compound WX_1 in water was about 110 times higher than that of the compound of formula (I), and the solubility performance was remarkably improved.

Solubility Study of the A Crystal Form of Compound WX_1 at Different pHs

Experimental Method:

About 10 mg of the A crystal form of compound WX_1 was added to an 8 mL glass vial, 9 replicates were weighed, and then 4 mL of different vehicles (0.1 N HCl, 0.01 N HCl, water, a pH 3.8 buffer, a pH 4.5 buffer, a pH 5.5 buffer, a pH 6.0 buffer, a pH 7.5 buffer, and a pH 6.8 buffer) were added respectively. A magnet was added to the above suspension, which was placed on a magnetic stirrer for stirring (temperature 37° C., dark). After respectively stirring for 4 hours and 24 hours, samples were taken and centrifuged, and the residual solids in the lower layers were tested by XRPD. The samples in the upper layers were filtered with a filtration membrane. The concentrations of the filtrates were determined by HPLC and the pHs were measured. After the HPLC system was equilibrated with a mobile phase, the analysis of the samples started. The results were as shown in the following table:

|  | pH | | State | | Solubility | | Description of |
| --- | --- | --- | --- | --- | --- | --- | --- |
|  | | | | | 4 hrs | (24 hrs) | |
| Vehicle | 4 hrs | 24 hrs | 4 hrs | 24 hrs | (mg/mL) | (mg/mL) | Solubility |
| 0.1N HCl (pH 1.00) | 1.05 | 1.05 | clear | clear | >2.5 | >2.5 | slightly soluble |
| 0.01N HCl (pH 1.99) | 2.29 | 2.32 | clear | clear | >2.5 | >2.5 | slightly soluble |
| pH 3.8 buffer (pH 3.80) | 3.98 | 3.97 | clear | clear | >2.5 | >2.5 | slightly soluble |
| pH 4.5 buffer (pH 4.48) | 4.47 | 4.47 | clear | clear | >2.5 | >2.5 | slightly soluble |
| pH 5.5 buffer (pH 5.52) | 5.32 | 5.31 | cloudy | cloudy | 0.110 | 0.138 | sparingly soluble |
| pH 6.0 buffer (pH 6.04) | 5.62 | 5.64 | cloudy | cloudy | 0.002 | 0.002 | practically insoluble |
| pH 6.8 buffer (pH 6.80) | 6.56 | 6.56 | cloudy | cloudy | <LOQ* | <LOQ | practically insoluble |
| pH 7.4 buffer (pH 7.39) | 7.12 | 7.11 | cloudy | cloudy | <LOQ | <LOQ | practically insoluble |
| purified water (pH 6.05) | 4.42 | 4.52 | cloudy | cloudy | 1.113 | 1.215 | slightly soluble |
| standard curve | | | | | y = 14412x + 6.8209, R2 = 1 | | |

*LOQ = 0.0003 mg/mL S/N = 21.7

Test of CDK2/4/6 Enzymatic Activity of the A Crystal Form of Compound WX_1

Experimental Materials:

CDK2/cyclin A, CDK4/cyclin D1, CDK6/cyclin D1 (Life technology). ULight-labeled polypeptide substrates ULight-4E-BP1 and ULight-MBP (PerkinElmer). Europium-labeled anti-myelin basic protein antibody and europium-labeled rabbit antibody (PerkinElmer). Envision Multilabel Plate Reader (PerkinElmer) was used for signal detection.

Experimental Method:

Three-fold dilution, including 10 concentration gradients, was performed on the compound to be tested, and the final concentration range was from 5 μM to 0.25 nM.

Enzyme Reaction System of CDK2/Cyclin A

The standard Lance Ultra method was performed by a 10 μL enzyme reaction system containing 0.5 nM CDK2/cyclin A protein, 100 nM ULight-MBP polypeptide, and 25 μM ATP. The dilutions of the compounds were dissolved in an enzyme buffer, respectively. The components of the buffer included 50 mM hydroxyethylpiperazine ethanesulfonic acid solution (pH 7.5), 1 mM ethylenediaminetetraacetic acid, 10 mM magnesium chloride, 0.01% Brij-35, and 2 mM dithiothreitol. After the reaction was started, an OptiPlate 384-well plate was sealed with a top heat-sealing film TopSeal-A and incubated at room temperature for 60 minutes.

Enzyme Reaction System of CDK4/Cyclin D1

The standard Lance Ultra method was performed by a 10 μL enzyme reaction system containing 0.3 nM CDK4/cyclin D1 protein, 50 nM ULight-4E-BP1 polypeptide, and 350 μM ATP. The dilutions of the compounds were dissolved in an enzyme buffer, respectively. The components of the buffer included 50 mM hydroxyethylpiperazine ethanesulfonic acid solution (pH 7.5), 1 mM ethylenediaminetetraacetic acid, 10 mM magnesium chloride, 0.01% Brij-35, and 2 mM dithiothreitol. After the reaction was started, an OptiPlate 384-well plate was sealed with a top heat-sealing film TopSeal-A and incubated at room temperature for 180 minutes.

Enzyme Reaction System of CDK6/Cyclin D1

The standard Lance Ultra method was performed by a 10 μL enzyme reaction system containing 0.8 nM CDK6/cyclin D1 protein, 50 nM ULight-4E-BP1 polypeptide, and 250 M ATP. The dilutions of the compounds were dissolved in an enzyme buffer, respectively. The components of the buffer included 50 mM hydroxyethylpiperazine ethanesulfonic acid solution (pH 7.5), 1 mM ethylenediaminetetraacetic acid, 10 mM magnesium chloride, 0.01% Brij-35, and 2 mM dithiothreitol. After the reaction was started, an OptiPlate 384-well plate was sealed with a top heat-sealing film TopSeal-A and incubated at room temperature for 180 minutes.

A stop buffer of the enzyme reaction was prepared, EDTA was dissolved in a 1-fold diluted detection buffer, and the reaction was terminated at room temperature for 5 minutes. 5 μL of the detection mixture (formulated with the europium-labeled anti-myelin basic protein antibody and the europium-labeled rabbit antibody, respectively) was added to the CDK2/cyclin A, CDK4/cyclin D1 and CDK6/cyclin D1 reaction systems, respectively. Incubation was carried out for 60 minutes at room temperature, and the reaction signals were detected using an Envision instrument according to the principle of time-resolved fluorescence resonance energy transfer.

Experimental Results:

The original data was converted to the inhibition rate using the equation (Max-Ratio)/(Max-Min)*100%, and the values of $IC_{50}$ were obtained by curve fitting using four parameters (obtained by the 205 mode in XLFIT5, iDBS). The results were as follows:

| Test compound | CDK4 $IC_{50}$ (nM) | CDK6 $IC_{50}$ (nM) | CDK2 $IC_{50}$ (nM) |
| --- | --- | --- | --- |
| Palbociclib | 5.23 | 0.98 | 1314.03 |
| LY2835219 | 1.02 | 1.22 | 14.73 |
| A crystal form of compound WX_1 | 0.35 | <0.80 | 2.43 |

Note: $IC_{50}$ referred to the corresponding concentration of a reagent when 50% maximal inhibition was produced by using the reagent.

Inhibition Assay of the A Crystal Form of WX_1 on MCF-7 Breast Cancer Cell Proliferation Experimental Materials:

RPMI 1640 medium, fetal bovine serum and penicillin/streptomycin as antibiotics were purchased from Promega (Madison, Wis.). The MCF-7 cell line was purchased from the European Collection of Authenticated Cell Cultures (ECACC). Envision MultiLabel Plate Reader (PerkinElmer).

Experimental Method:

MCF-7 cells were seeded in a black 384-well plate with 45 μL of cell suspension (containing 200 MCF-7 cells) per well. The cell plate was placed in a carbon dioxide incubator for overnight culture.

The test compounds were diluted 3 times to the 10th concentration with Bravo, i.e., diluted from 10 μM to 0.508 nM, and a duplicate-well experiment was set. The medium was added to the middle plate in an amount of 49 μL per well. The gradient-diluted compounds were transferred in an amount of 1 μL per well to the middle plate according to the corresponding positions, and the mixture was mixed evenly and transferred to the cell plate in an amount of 5 μL per well. The cell plate was incubated in a carbon dioxide incubator for 6 days.

Promega CellTiter-Glo reagent was added to the cell plate in an amount of 25 pt per well, and incubated for 10 minutes at room temperature to stabilize the luminescence signal. Reading was performed using a PerkinElmer Envision Multilabel Plate Reader.

Experimental Results:

The original data was converted to the inhibition rate using the equation (Max-Ratio)/(Max-Min)*100%, and the values of $IC_{50}$ were obtained by curve fitting using four parameters (obtained by the 205 mode in XLFIT5, iDBS). The results were as follows:

| Test compound | MCF-7 $IC_{50}$ (nM) |
|---|---|
| Palbociclib | 88.23 |
| LY2835219 | 184.83 |
| A crystal form of WX_1 | 70.03 |

Experimental Conclusion:

The A crystal form of compound WX_1 of the present disclosure had significant inhibitory activity against the proliferation of the estrogen receptor-positive MCF-7 breast cancer cells. The A crystal form of compound WX_1 had higher inhibitory activity against MCF-7 cell proliferation than the reference compounds Palbociclib and LY2835219.

Inhibition Assay of the Compound of Formula (I) on the Proliferation of MCF-7 Cells and MDA-MB-436 Cells Experimental Materials:

RPMI 1640 medium, fetal bovine serum and penicillin/streptomycin as antibiotics were purchased from Promega (Madison, Wis.). The MCF-7 cell line and the MDA-MB-436 cell line were purchased from the European Collection of Authenticated Cell Cultures (ECACC). Envision Multilabel Plate Reader (PerkinElmer).

Experimental Method:

MCF-7 cells were seeded in a black 384-well plate with 45 μL of cell suspension (containing 200 MCF-7 cells) per well. The cell plate was placed in a carbon dioxide incubator for overnight culture.

MDA-MB-436 cells were seeded in a black 384-well plate with 45 μL of cell suspension (containing 585 MDA-MB-436 cells) per well. The cell plate was placed in a carbon dioxide incubator for overnight culture.

The test compounds were diluted 3 times to the 10th concentration with Bravo, i.e., diluted from 10 μM to 0.508 nM, and a duplicate-well experiment was set. The medium was added to the middle plate in an amount of 49 μL per well. The gradient-diluted compounds were transferred in an amount of 1 μL per well to the middle plate according to the corresponding positions, and the mixture was mixed evenly and transferred to the cell plate in an amount of 5 μL per well. The cell plate was incubated in a carbon dioxide incubator for 6 days.

Promega CellTiter-Glo reagent was added to the cell plate in an amount of 25 μL per well, and incubated for 10 minutes at room temperature to stabilize the luminescence signal. Reading was performed using a PerkinElmer Envision Multilabel Plate Reader.

Experimental Results:

The original data was converted to the inhibition rate using the equation (Max-Ratio)/(Max-Min)*100%, and the values of $IC_{50}$ were obtained by curve fitting using four parameters (obtained by the 205 mode in XLFIT5, iDBS). The results were as follows:

| Test compound | MCF-7 $IC_{50}$ (nM) | MDA-MB-436 $IC_{50}$ (nM) |
|---|---|---|
| compound of formula (a) | 240 | 2098 |
| compound of formula (I) | 32.1 | 328 |

In Vivo Drug Efficacy Study of the A Crystal Form of Compound WX_1 (I)

Experimental Materials:

Cell line-derived xenograft (CDX) BALB/c nude mice that were female, 6- to 8-week old, weighed 20 g, and subcutaneously implanted with human tumor cell line derived from MCF-7 breast cancer patients were used. A total of 150 mice were needed, which were purchased from Beijing Vital River Laboratory Animal Technology Co., Ltd.

Experimental Purpose:

To evaluate the in vivo drug efficacy of the test drugs Palbociclib, LY2835219 and the A crystal form of compound WX_1 in a human breast cancer MCF-7 subcutaneous xenograft tumor model Experimental Method:

(1) Detailed Scheme for Formulating Drugs:

| Compound | Formulating method | Concentraion (mg/mL) | Storage condition |
|---|---|---|---|
| vehicle (0.5% methyl cellulose) | 5 g of methyl cellulose was weighed and placed in a 1000 mL glass vial, 1000 mL of deionized water was added, and the mixture was vortexed until the solution was clear. | — | 4° C. |
| 50 mmol/L sodium lactate buffer | 2.069 mL of lactic acid was dissolved in 200 mL of deionized water, and the pH was adjusted to 4.0 with 5N NaOH. The solution was transferred to a 500 mL volumetric flask, diluted to a volume of 500 mL by adding deionized water, and the solution was filtered with a 0.2 μm filter head. | — | 4° C. |
| Palbociclib | 60.91 mg of Palbociclib was weighed and placed in a brown vial, and 21 mL of 50 mmol/L sodium lactate buffer (pH = 4) was added. | 2.5 | 4° C. |
| Palbociclib | 121.81 mg of Palbociclib was weighed and placed in a brown vial, and 21 mL of 50 mmol/L sodium lactate buffer (pH = 4) was added. | 5 | 4° C. |
| LY2835219 | 64.87 mg of LY2835219 was weighed and placed in a brown vial, 21 mL of 0.5% MC was added, and the mixture was vortexed to a homogeneous solution. | 2.5 | 4° C. |

-continued

| Compound | Formulating method | Concentraion (mg/mL) | Storage condition |
|---|---|---|---|
| A crystal form of compound WX_1 | 49.77 mg of the A crystal form of compound WX_1 was weighed and placed in a brown vial, 21 mL of 0.5% MC was added, and the mixture was vortexed to a homogeneous solution. | 1.875 | 4° C. |

Note: The drugs needed to be mixed gently and thoroughly before animal administration.

(2) Grouping and Dosing Schedules of the Animal Experiment:

| Group | N1 | Compound used for treatment | Dosage (mg/kg) | Parameter of administration volume (μl/g) | Administration route | Administration frequency |
|---|---|---|---|---|---|---|
| 1 | 10 | solvent control | — | 10 | PO | QD × 3W |
| 2 | 10 | Palbociclib | 25 | 10 | PO | QD × 3W |
| 3 | 10 | Palbociclib | 50 | 10 | PO | QD × 3W |
| 4 | 10 | LY2835219 | 25 | 10 | PO | QD × 3W |
| 5 | 10 | A crystal form of compound WX_1 | 18.75 | 10 | PO | QD × 3W |

(3) Experimental Procedures:

BALB/c nude mice that were female, 6- to 8-week old, and weighed approximately 20 g were used. The mice were maintained in separate ventilated cages (10 mice per cage) in a special pathogen-free environment. All the cages, bedding and water were disinfected prior to use. All the animals were free to access a standard certified commercial laboratory diet. A total of 150 mice were purchased from Beijing Vital River Laboratory Animal Technology Co., Ltd. for research. Each mouse was implanted subcutaneously with an estrogen tablets (0.18 mg/tablet, 60-day sustained release) in the left back. After 3 days, each mouse was implanted with tumor cells (10×10$^6$ in 0.2 mL of phosphate buffer) subcutaneously in the right back for tumor growth. Administration was started when the average tumor volume reached about 150 to 200 mm$^3$. The test compounds were orally administered daily, and the administration dosages were as shown in the above table. The tumor volumes were measured twice a week using a two-dimensional caliper. The volumes were expressed in cubic millimeters and calculated by the following formula: V=0.5 a×b$^2$, wherein a and b were the long diameter and short diameter of a tumor, respectively. The anti-tumor efficacy was determined by dividing the average increase of the tumor volumes of the animals treated with a compound by the average increase of the tumor volumes of the animals without being treated with the compound.

Experimental Results:

The antitumor efficacy of the test compounds was as follows:

| | Administration | Tumor volume (mm$^3$) | | | |
|---|---|---|---|---|---|
| Test compoumd | dosage (mg/kg) | Day 0 | Day 7 | Day 14 | Day 20 |
| Vehicle | 0 | 153 | 231 | 356 | 537 |
| Palbociclib | 25.0 | 153 | 203 | 252 | 222 |
| Palbociclib | 50.0 | 153 | 180 | 197 | 137 |
| LY2835219 | 25.0 | 153 | 155 | 147 | 102 |
| A crystal form of compound WX_1 | 18.75 | 153 | 156 | 136 | 98 |

Experimental Conclusion:

The A crystal form of compound WX_1 of the present disclosure exhibited significant anti-tumor activity on MCF-7 breast cancer based on a human tumor cell line-derived xenograft (CDX) model. As shown in the above table, 20 days after the start of the experiment, the tumor volume of the animal group without administration increased rapidly from the initial 153 mm$^3$ to 537 mm$^3$, while the tumor volume of the animal group with administration of the A crystal form of compound WX_1 during the same period only decreased from the initial 153 mm$^3$ to 98 mm$^3$, which was significantly smaller than the tumor volumes of the groups to which the reference compounds Palbociclib and LY2835219 were administered. Considering the fact that the administration dosage of the A crystal form of compound WX_1 (18.75 mg/kg) was lower than that of the reference compound LY2835219 (25 mg/kg) or the reference compound Palbociclib (25 mg/kg, 50 mg/kg) (high dose of Palbociclib was experimentally proved to be intolerable), the anti-tumor activity of the A crystal form of compound WX_1 was significantly superior to the reference compounds.

In Vivo Drug Efficacy Study of the A Crystal Form of Compound WX_1 (II)

Experimental Materials:

Cell line-derived xenograft (CDX) BALB/c nude mice that were female, 6- to 8-week old, weighed 17 to 20 g, and subcutaneously implanted with human tumor cell line derived from LU-01-0393 lung cancer patient were used. A total of 72 mice were needed and were purchased from Shanghai Xipuer-Bikai Experimental Animal Co., Ltd. Human lung cancer LU-01-0393 tumor (i.e., non-small cell lung cancer) was originally derived from a clinical sample of a surgical resection. It was defined as passage P0 after being inoculated to nude mice, and the tumor of passage P0 was re-inoculated to nude mice and was then defined as passage P1, and so forth. Passage was performed in nude mice. LU-01-0393-FP5 was obtained from the transplantation after the recovery of P4. This study would use the tumor tissue of passage FP6.

Experimental Purpose:

To evaluate the in vivo drug efficacy of the test drugs Palbociclib, LY2835219 and the A crystal form of compound WX_1 in a human lung cancer LU-01-0393 subcutaneous xenograft tumor model.

Experimental Method:

(1) Detailed Scheme for Formulating Drugs:

| Compound | Formulating method | Concentration (mg/mL) | Storage condition |
|---|---|---|---|
| Vehicle (0.5% methyl cellulose) | 5 g of methyl cellulose was weighed and placed in a 1000 mL glass vial, 1000 mL of deionized water was added, and the mixture was vortexed until the solution was clear. | — | 4° C. |

-continued

| Compound | Formulating method | Concentration (mg/mL) | Storage condition |
|---|---|---|---|
| 50 mmol/L sodium lactate buffer | 2.069 mL of lactic acid was dissolved in 200 mL of deionized water, and the pH was adjusted to 4.0 with 5N NaOH. The solution was transferred to a 500 mL volumetric flask, diluted to a volume of 500 mL by adding deionized water, and the solution was filtered with a 0.2 μm filter head. | — | 4° C. |
| Palbociclib | 267.27 mg of Palbociclib was weighed and placed in a brown vial, 19 mL of 50 mmol/L sodium lactate buffer (pH = 4) was added, and the mixture was sonicated and vortexed to obtain a homogenous and transparent solution. | 12 | 4° C. |
| LY2835219 | 283.37 mg of LY2835219 was weighed and placed in a brown vial, 19 mL of 0.5% methyl cellulose was added, and the mixture was sonicated and vortexed to obtain a homogenous and transparent solution. | 12 | 4° C. |
| A crystal form of compound WX_1 | 108.94 mg of the A crystal form of compound WX_1 was weighed and placed in a brown vial, 19 mL of 0.5% methyl cellulose was added, and the mixture was sonicated and vortexed to obtain a homogenous and transparent solution | 4.5 | 4° C. |

Note: The drugs needed to be mixed gently and thoroughly before animal administration.

(2) Grouping and Dosing Schedules of Animal Experiment:

| Group | N1 | Compound used for treatment | Dosage (mg/kg) | Parameter of administration volume (μl/g) | Administration route | Administration frequency |
|---|---|---|---|---|---|---|
| 1 | 10 | solvent control | — | 10 | PO | QD × 3W |
| 2 | 10 | Palbociclib | 120 | 10 | PO | QD × 3W |
| 3 | 10 | LY2835219 | 120 | 10 | PO | QD × 3W |
| 4 | 10 | A crystal form of compound WX_1 | 45 | 10 | PO | QD × 3W |

(3) Experimental Procedures:

BALB/c nude mice that were female, 6- to 8-week old, and weighed approximately 17 to 20 g were used. The mice were maintained in separate ventilated cages in a special pathogen-free environment. All the cages, bedding and water were disinfected prior to use. All the animals were free to access a standard certified commercial laboratory diet. A total of 72 mice purchased from Shanghai Xipuer-Bikai Experimental Animal Co., Ltd. were used for the study. The LU-01-0393 FP6 tumor tissue was cut to 20 to 30 mm³ and inoculated to the right back of each mouse to wait for the tumor growth. When the average tumor volume reached about 171 mm³, the mice were randomized into groups and administered. The test compounds were orally administered daily, and the administration dosages were as shown in the above table. The tumor diameters were measured twice a week using a two-dimensional caliper. The tumor volumes were calculated by the following formula: V=0.5 a×b², wherein a and b were the long diameter and the short diameter of a tumor, respectively. The anti-tumor efficacy was determined by dividing the average increase of the tumor volumes of the animals treated with a compound by the average increase of the tumor volumes of the animals without being treated with the compound.

Experimental Results:

The antitumor efficacy of the test compounds was as follows:

| Test compound | Administration dosage (mg/kg) | Tumor volume (mm³) | | | |
|---|---|---|---|---|---|
| | | Day 0 | Day 7 | Day 14 | Day 21 |
| Vehicle | 0 | 172 ± 26 | 337 ± 45 | 486 ± 63 | 731 ± 80 |
| Palbociclib | 120.0 | 170 ± 24 | 261 ± 38 | 266 ± 41 | 251 ± 34 |
| LY2835219 | 120.0 | 172 ± 23 | 228 ± 26 | 255 ± 30 | 272 ± 36 |
| A crystal form of compound WX_1 | 45 | 171 ± 26 | 172 ± 33 | 150 ± 29 | 175 ± 42 |

What is claimed is:

1. A crystal form of a maleate salt of formula (II)

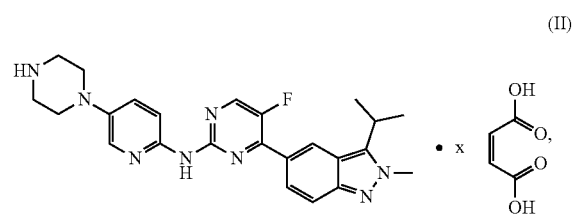

(II)

wherein x is 1, and an X-ray powder diffraction spectrum of the crystal form has characteristic diffraction peaks at the following 2θ angles: 4.69±0.2° and 14.04±0.2°.

2. The crystal form according to claim 1, wherein the X-ray powder diffraction spectrum of the crystal form has characteristic diffraction peaks at the following 2θ angles: 4.69±0.2°, 9.35±0.2°, 13.28±0.2°, 14.04±0.2°, 16.03±0.2°, 18.74±0.2°, 20.08±0.2°, and 28.25±0.2°.

3. The crystal form according to claim 1, wherein a differential scanning calorimetry curve of the crystal form has an endothermic peak at 208.18° C.±3° C.

4. The crystal form according to claim 1, wherein a thermogravimetric analysis curve of the crystal form displays a weight loss of 0.3110±0.2% at 188.49±3° C.

5. A preparation method of the crystal form according to claim 1, comprising the following steps:
   (1) mixing maleic acid with a solvent;
   (2) adding the compound of formula (I) to the mixture of step (1); and
   (3) filtering and drying;
   wherein the solvent is selected from one or more of methanol, ethanol, isopropanol, acetone, and ethyl acetate, and a methanol/water mixed solvent or an isopropanol/water mixed solvent.

6. A crystal form of the compound of formula (I),

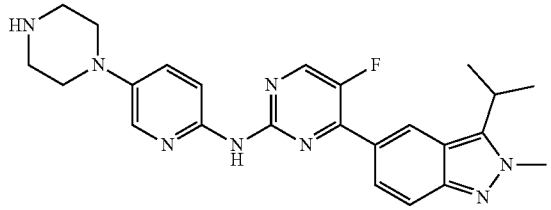 [SMILES: CC(C)c1c2cc(-c3nc(Nc4ccc(N5CCNCC5)cn4)ncc3F)ccc2nn1C]

wherein an X-ray powder diffraction spectrum of the crystal form has characteristic diffraction peaks at the following 2θ angles: 12.88±0.2°, 14.18±0.2°, 16.72±0.2°, 17.49±0.2°, 19.21±0.2°, 21.06±0.2°, 21.65±0.2°, and 24.14±0.2°.

7. The crystal form according to claim 6, wherein a differential scanning calorimetry curve of the crystal form has an endothermic peak at 225.76° C.

8. A pharmaceutical composition, comprising a therapeutically effective amount of the crystal form according to claim 1, and a pharmaceutically acceptable adjuvant.

9. A pharmaceutical composition, comprising a therapeutically effective amount of the crystal form according to claim 6, and a pharmaceutically acceptable adjuvant.

10. A method for treating a mammalian CDK4/6-mediated disease, wherein the CDK4/6-mediated disease is breast cancer or lung cancer, and the method comprises administrating a therapeutically effective amount of the crystal form according to claim 1 to a mammal, and said treating excludes preventing.

11. A method for treating a mammalian CDK4/6-mediated disease, wherein the CDK4/6-mediated disease is breast cancer or lung cancer, and the method comprises administrating a therapeutically effective amount of the crystal form according to claim 6 to a mammal, and said treating excludes preventing.

12. A method of preparing the crystal form according to claim 6,
(i) adding the compound of formula (I) to a solvent to form a mixture, and stirring the mixture at a temperature of 70 to 100° C. for 0.5 to 2 hours;
(ii) cooling the mixture, and allow the mixture to stand for 8 to 16 hours to form a crystal; and
(iii) isolating the crystal;
wherein the solvent is a mixed solvent of ethanol and water, and a volume ratio of ethanol to water is 3:1.

13. The crystal form according to claim 1, wherein the X-ray powder diffraction spectrum of the crystal form has characteristic diffraction peaks at the following 2θ angles: 4.69±0.2°, 9.35±0.2°, 10.01±0.2°, 13.28±0.2°, 14.04±0.2°, 16.03±0.2°, 18.74±0.2°, 20.08±0.2°, 23.53±0.2°, 25.11±0.2°, 27.80±0.2°, and 28.25±0.2°.

14. The crystal form according to claim 13, wherein the X-ray powder diffraction spectrum of the crystal form has characteristic diffraction peaks at the following 2θ angles: 4.69±0.2°, 9.35±0.2°, 10.01±0.2°, 13.28±0.2°, 14.04±0.2°, 16.03±0.2°, 16.83±0.2°, 17.73±0.2°, 18.58±0.2°, 18.74±0.2°, 20.08±0.2°, 21.58±0.2°, 23.53±0.2°, 25.11±0.2°, 25.27±0.2°, 27.80±0.2°, 28.25±0.2°, and 33.00±0.2°.

15. The crystal form according to claim 6, wherein the X-ray powder diffraction spectrum of the crystal form has characteristic diffraction peaks at the following 2θ angles: 9.86±0.2°, 12.88±0.2°, 14.18±0.2°, 16.72±0.2°, 17.49±0.2°, 19.21±0.2°, 21.06±0.2°, 21.65±0.2°, 24.14±0.2°, 26.29±0.2°, and 27.69±0.2°.

16. The crystal form according to claim 15, wherein the X-ray powder diffraction spectrum of the crystal form has characteristic diffraction peaks at the following 2θ angles: 9.56±0.2°, 9.86±0.2°, 11.53±0.2°, 12.01±0.2°, 12.88±0.2°, 14.18±0.2°, 15.21±0.2°, 15.66±0.2°, 16.72±0.2°, 17.49±0.2°, 18.79±0.2°, 19.21±0.2°, 19.76±0.2°, 21.06±0.2°, 21.65±0.2°, 22.52±0.2°, 22.93±0.2°, 24.14±0.2°, 24.47±0.2°, 26.29±0.2°, 27.69±0.2°, 28.48±0.2°, 28.79±0.2°, 30.25±0.2°, 30.74±0.2°, 31.67±0.2°, 34.79±0.2°, and 35.18±0.2°.

* * * * *

UNITED STATES PATENT AND TRADEMARK OFFICE
CERTIFICATE OF CORRECTION

PATENT NO. : 10,626,107 B2
APPLICATION NO. : 16/331915
DATED : April 21, 2020
INVENTOR(S) : Charles Z. Ding et al.

Page 1 of 1

It is certified that error appears in the above-identified patent and that said Letters Patent is hereby corrected as shown below:

In the Claims

Column 30, Line 27: In Claim 1, delete "formula (II)" and insert -- formula (II), -- therefor.

Column 30, Line 43: In Claim 1, delete "20" and insert -- 2θ -- therefor.

Column 30, Line 46: In Claim 2, delete "20" and insert -- 2θ -- therefor.

Column 31, Line 15: In Claim 6, delete "20" and insert -- 2θ -- therefor.

Column 32, Line 13: In Claim 13, delete "20" and insert -- 2θ -- therefor.

Column 32, Line 18: In Claim 14, delete "20" and insert -- 2θ -- therefor.

Column 32, Line 26: In Claim 15, delete "20" and insert -- 2θ -- therefor.

Column 32, Line 31: In Claim 16, delete "20" and insert -- 2θ -- therefor.

Signed and Sealed this
Fourteenth Day of July, 2020

Andrei Iancu
*Director of the United States Patent and Trademark Office*